US005682882A

United States Patent [19]

Lieberman

[11] Patent Number: 5,682,882

[45] Date of Patent: Nov. 4, 1997

[54] VIGILANCE MONITOR SYSTEM

[76] Inventor: Harris R. Lieberman, 21 Canoe River Rd., Sharon, Mass. 02067

[21] Appl. No.: 430,678

[22] Filed: Apr. 28, 1995

[51] Int. Cl.[6] .................... A61B 5/00

[52] U.S. Cl. .................... 128/630; 128/745; 128/746; 128/774

[58] Field of Search .................... 128/733, 774, 128/782

[56] References Cited

U.S. PATENT DOCUMENTS

| | | | |
|---|---|---|---|
| 4,461,301 | 7/1984 | Ochs | 128/733 |
| 5,277,197 | 1/1994 | Church et al. | 128/733 |
| 5,522,386 | 6/1996 | Lerner | 128/733 |

OTHER PUBLICATIONS

Colburn, et al., Man in Transit: Biochemical and Physiological changes during intercontinental flights, Lancet, 1, 977–980 (1976).

Graeber, R.C. (1988), Aircrew Fatigue and Circadian Rhythmicity, Human Factors in Aviation Ed., Wiener and Nagel, Academic Press, San Diego, pp. 305–344.

Krueger, P. (1989), Sustained work, fatigue, sleep loss and performances: A review of the issues. Work & Stress, 3(2), 129–141.

Lieberman, H.R., et al. (1989), Circadian rhythms of activity in healthy young and elderly humans. Neurobiology of Aging, 10, 259–265.

Mackie, R.R. (1987), Vigilance Research—Are we ready for countermeasures? Human Factors, 29(6), 707–723.

Mitler, M.M. (1988), Catastrophes, Sleep and Public Policy: Consensus Report. Sleep, 11(1).

Teicher, M.H., et al. (1988), Altered Circadian activity rhythms in geriatric patients with major depression. Archives of General Psychiatry, 45, 913–917.

Redmond, D.P., et al. (1985), Observations on the design and specification of a wrist-worn human activity monitoring system. Behavior Research Methods, Instruments & Computers, 17(6), 659–669.

Wiener, E.L., Cockpit Automation, Human Factors in Aviation Ed., Weiner et al., Academic Press, San Diego, pp. 433–461 (1988).

*Primary Examiner*—Vincent Millin
*Assistant Examiner*—Robert N. Wieland
*Attorney, Agent, or Firm*—John Francis Moran

[57] ABSTRACT

This invention includes a plurality of ambient sensors at least one human subject stimulator, at least one sensor adapted to detect the human subject response to the stimuli, and a controller programmed to receive information from the environmental or ambient sensors, to control the stimulators, and to record the human subject's response to the stimuli via the human response sensors. The invention can monitor and record, over a series of consecutive time periods, the human subject's vigilance, level of physical activity, and other physiological, physical, and chemical variables pertaining to the subject and his or her ambient environment. The invention can be used to prevent impairments in mental performance occurring due to fatigue or exposure to adverse environmental conditions or human subject condition. Based on continuous evaluations of the status of the subject (and if so desired, the ambient environment) the vigilance monitor can be programmed to automatically intervene to prevent degradation in mental performance by providing a warning to the subject or to others.

40 Claims, 17 Drawing Sheets

VIGILANCE MONITOR SYSTEM

STATEMENT AS TO RIGHTS OF INVENTION MADE BY GOVERNMENT EMPLOYEES

This invention was made by a government employee. The United States Army, as represented by the Secretary of the Army, has determined pursuant to 37 CFR Part 501 to retain certain rights in this invention.

TECHNICAL FIELD

Alertness and vigilance of human operators, monitors, and guards over long periods of time can be critical for the safe operation of a variety of equipment, including, for example, transportation vehicles. Operator alertness and vigilance is also important in the efficient and safe monitoring of various industrial processes and numerous critical military tasks. Even highly motivated, well-trained individuals are unable to sustain optimum levels of alertness when they are required to be alert for long periods of time. When individuals are required to remain awake and alert during times when they are normally asleep (i.e., late evening, nighttime, and early morning hours), maintaining alertness and responding appropriately to the external environment becomes difficult. Individuals responsible for operating critical equipment such as power plants, heavy machinery, and public and private vehicles, including aircraft or military weapons for sustained periods of time frequently have lapses of attention and can even fall asleep while on duty. The consequences of fatigue and lapses in vigilance can be tragic not only for the responsible individual but also for passengers and the public at large. Appropriate preservatives and countermeasures for such lapses are often not available when the individuals in question are responsible for the operation or guidance of military equipment, commercial airliners, nuclear power plants, and other security systems.

Sustained vigilance is necessary for a variety of tasks including such military tasks as sentry duty, sonar and radar monitoring, and standing watch, and is essential in countless other operational settings. Personnel may be subject to surveillance or monitoring to avoid potentially catastrophic events. Adverse exposure to environmental conditions including high altitude, heat, cold, etc. may exacerbate reductions in alertness and vigilance attributable to normal day/night variations in mental alertness. Increased automation in many of these activities reduces the moment-by-moment demands on the individual and thereby temporarily increases boredom whereupon maintenance of alertness becomes more difficult.

Unobtrusive ambulatory devices for detailed monitoring of human vigilance are currently not available. Ambulatory devices capable of detecting actual psychological states of the individual to assess vigilance are also unavailable to intervene and prevent performance degradation or the onset of sleep or loss of vigilance.

Prior art monitoring activity monitors are described in U.S. Pat. Nos. 4,353,375 and 5,197,489 which record activity over specified blocks of time. However, they have no capability to record mental performance or intervene to modify human performance.

Other devices indirectly monitor vigilance by measuring physical position of the eyelid or head position and sound an alarm if a change in alertness is inferred. Such devices are incapable of monitoring directly human performance and cannot store data. They are unable to monitor ambient environmental conditions and do not employ a combination of inputs to modify vigilance. They are incapable of assessing levels of activity of processing such information and are incapable of intervening to assess decrements in alertness. Further, such apparatuses are believed incapable of taking into account the previous individual history of the wearer or the time of day or other conditions which could be used to optimize performance.

Circadian desynchronization is a related but separate problem. The present invention may be adapted to treat and correct circadian desynchronization. Circadian desynchronization occurs when individuals alter their typical daily activities and pattern of sleep; this often appears as jet lag.

Certain medical conditions such as blindness or central nervous system disease including Alzheimer's disease, also contribute to circadian desynchronization by upsetting the normal human rhythms of rest and activity.

SUMMARY OF THE INVENTION

The present invention is directed to an activity and alertness monitor which includes a stimulation and reaction detection function, and the capability of storing the stimulation/reaction information. The stimulation/reaction functions enable active intervention to interrupt degradation in vigilance and restore alertness. Signalling to third parties is contemplated for warning of failure or incipient failure.

Under control of a microprocessor-based controller, including data and program storage, information is collected from the ambient environment via an initial series of sensors. Additionally, the controller generates (under program control) certain stimuli which are transmitted to a human subject via stimulators and the reaction responses to these stimuli are sensed and returned to the controller by sensors. The controller controls all functions including keeping track of the time at which they occur and is adaptable to increase or decrease the number of stimulations depending on ambient conditions, time of day, history of the wearer, etc.

A primary object of the invention is to monitor the alertness and vigilance of human subjects and to detect degradations in such vigilance which may affect performance. Another object of the invention is to monitor ambient environmental conditions which would under ordinary circumstances be expected to contribute to decreased vigilance of the human subject. Another object of the invention is to automatically intervene and provide a warning to the wearer or others of degradation in mental performance of the wearer.

Another object of the invention is to warn individuals of lapses in their alertness via direct stimuli and to warn supervisors or other employees of degradation in alertness directly as by an audible tone, visual signal, or other stimuli or signal. These warnings may be telemetered to a location remote from the site of the wearer. Another object of the invention is to continuously record information related to the actual environmental conditions such as temperature, humidity, ambient illumination, sound levels, altitude, and so forth, which may affect human vigilance.

Another object of the invention is to control synchronization of human activity rhythms (circadian rhythms) to the external environment by regulating rest and alertness cycles.

Another object of the invention is to monitor and record for later evaluation the performance of personnel during operations requiring sustained vigilance without supervision. Examples of such personnel functions include sentries and night watchmen, so that supervisors and management personnel can be certain that individuals are regularly performing their assigned duties.

Another object of the invention is to monitor effects of environmental factors such as light, sound, and pollutants, and their effect on human vigilance, reaction time, motor activity, and circadian rhythms. Another object of the invention is to enable selection prior to assignment of individuals with necessary personal vigilance characteristics for critical operational duties requiring maintenance of vigilance for long periods of time. Another object of the invention is to identify for treatment and to treat various medical conditions where inappropriate activity occurs, or when activity occurs at incorrect times.

Advantages of the invention include its portability, lightweight nature, generally permanent recording of data, increased information gathering ability regarding ambient environmental conditions, ability to intervene and minimize vigilance degradation, and capability to output stored data to larger computers and data storage devices.

The present vigilance monitor system can directly assess and record vigilance, defined as behavioral responsiveness to auditory or other physical human stimuli, rather than assessing an indirect measure of vigilance such as eye closure or head position. It is advantageous that the vigilance monitoring system will function regardless of the physical position of the subject or the activities in which the wearer is engaged. The vigilance monitor system will not interfere with the subject's vision.

The present invention is adaptable to regularize the functions of rest and activity and to speed adjustment to new schedules when needed. Other medical conditions associated with inappropriate patterns of rest and activity can be treated with this invention; examples include the syndromes of narcolepsy and somnambulism.

Another advantage of the present invention is that it can intervene to increase vigilance based on the individual's responsiveness to external stimuli. For example, if a failure to respond to a directed stimulus occurs, the vigilance monitor system can increase the intensity and/or vary other parameters of the warning alarm until a response has been elicited or a warning signalled.

Another advantage of the invention is that it can assess and maintain vigilance based on a combination of inputs including, but not limited to: motor activity of the individual subject, environmental conditions, and the responsiveness of the individual subject to stimuli generated by the vigilance monitor system. Still another advantage of the invention is that it is sensitive to various parameters, which it is capable of assessing and weighing, in combination with individual factors which can be varied depending on the desired use.

It is another advantage of the invention that environmental conditions can be monitored and if desired, the properties and behavior of the wearer of the device appropriately modified in response to changing environmental conditions before their effect might otherwise be detected. For example but not limitation, the occurrence or presence of extreme environmental conditions can be used to provide more frequent stimuli or to check temperature or temperature variations more often. Similarly, detection of such environmental or ambient conditions can initiate the signalling of an audible or visible (or both) alarm to warn the wearer of potentially dangerous environmental conditions.

Another advantage of the vigilance monitor system is that the physical activity of the wearer and the environmental conditions can be monitored simultaneously and the wearer can be prompted to alter his activity or change environmental conditions for safety or other reasons.

Another advantage of the vigilance monitor system is that the timing of the external actions of the device, and in particular the time periods when vigilance is assessed and modified by presentation of external stimuli, can be predetermined and selected prior to its deployment for use in a given situation. Thus, the device can increase vigilance for certain preset times of the day or night or in response to combinations of ambient environmental conditions.

Another feature of the invention is that spontaneous motor activity emitted by the wearer can be modified to increase or decrease such activity by sounding an alerting tone. The vigilance monitor system is a compact, self-contained unit capable of continuous monitoring and recording certain aspects of human behavior, in particular vigilance, reaction time, mental and psychomotor performance, and patterns of activity of the wearer, in addition to continuous assessment of a variety of ambient environmental conditions relevant to the mental and physical performance and health and welfare of the wearer. It is advantageous that the device is completely self-contained, requiring no external input to perform any of its functions after initialization.

Overall operation of the device is controlled by an internal microprocessor having sufficient logic and data analysis capabilities to independently perform all internal control functions, including acquisition of data from the external environment, processing of that data, and providing appropriate instructions to various sensors and output devices. On-board memory such as static read and write memory, should be available to perform complex control and analysis processes and to store information collected continuously for an extended period of time. An accurate real-time clock may be included to govern internal timekeeping functions and to aid in control of external output signals. Provision is made for storage of instructions governing the actions of the device; these may be transferred to it through an interface port from an external computer in the form of a computer program which is then executed by the microprocessor.

BRIEF DESCRIPTION OF THE DRAWING FIGURES

With the foregoing and other objects, features, and advantages of the invention that will become hereinafter apparent, the nature of the invention may be more clearly understood by reference to the following detailed description of the invention, the appended claims and to the several views illustrated in the attached drawings.

DETAILED DESCRIPTION OF THE PREFERRED EMBODIMENT

Figure 1:
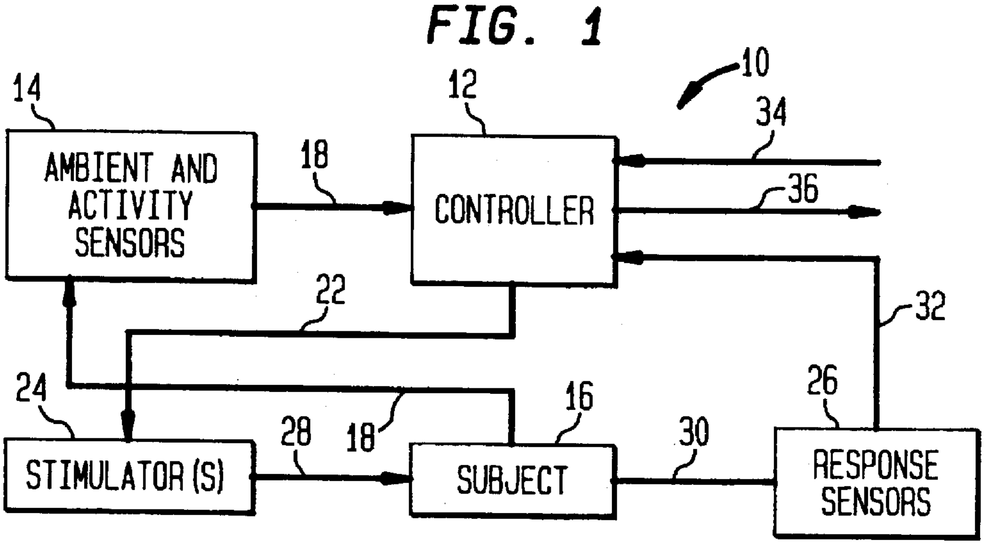
FIG. 1 is a simplified functional block diagram of the vigilance monitor system according to the present invention.

A block diagram of the vigilance monitor system 10 is provided in FIG. 1. A microprocessor contained in a controller 12 receives ambient environmental information input from sensors 14 and information regarding movement, position, or other activity on the part of the human subject wearer 16 along communications line 18. The human subject activity indications, if desired, are communicated 18 to controller 12, via ambient sensors 14. The present invention comprehends that such sensors will be included in wrist-mounted monitor housing or may be attached to the subject or the clothing or equipment of the subject 16. Controller 12 communicates via controller-to-stimulator signal path 22 to stimulators 24 to direct the various stimuli presented to the human subject. The stimuli are communicated directly to the subject 16 via generic path 28. Responsive to the stimuli a plurality of response sensors 26 detect and receive via path 30 the human subject responses to the stimuli from stimulator(s) 24. Response sensors 26 produce one or more output signals passed along response sensor/controller line 32 to communicate the subject's responses to the controller 12. One or more input signal lines 34 are provided for initial programming and periodic external updates to the program instruction set stored in controller 12. One or, more output signal lines 36 are provided to download the content of the stored information, as described in greater detail hereinafter.

Figure 2:
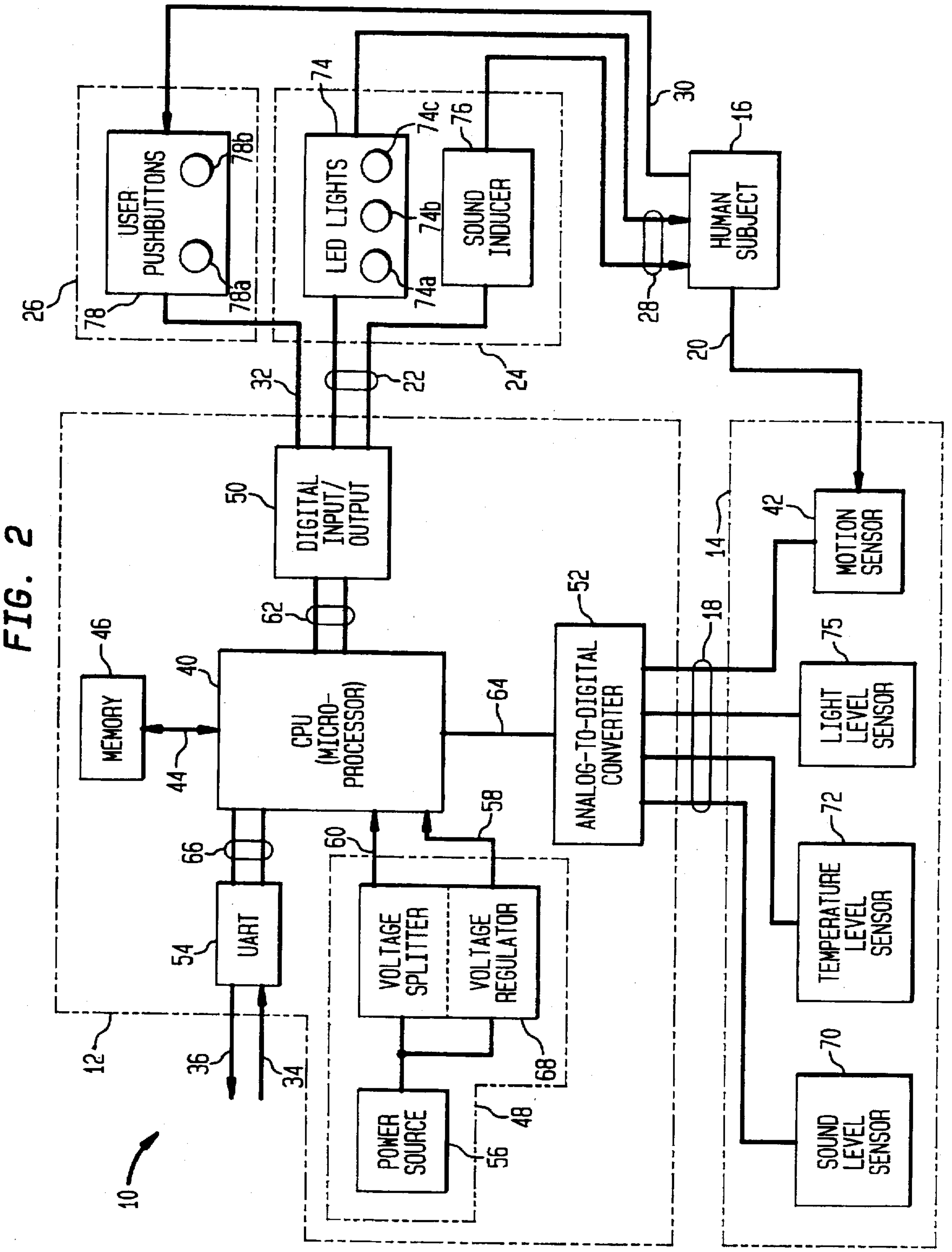
FIG. 2 is a detailed functional block diagram of the vigilance monitor system according to FIG. 1.

Turning now to FIG. 2, a more detailed block diagram of the vigilance monitor system of the present invention 10, there are shown a controller 12, a plurality of the ambient and activity sensors 14, a subject 16, an ambient sensor controller signal line 18 communicating the sensed ambient signals to controller 12, a subject sensor path 20 communicating sensed activity of the subject 16 to the controller 12 via motion sensor 42 to be described hereinafter, a controller stimulator line 22 which may comprise a plurality of individual signal lines or a single signal line, a plurality of stimulators 24, at least one stimulation path 28 extending between the stimulators and the subject 16, a response path 30 by which the subject 16 may communicate his response to controller 12, response sensor-to-controller signal lines 32 which may be a single or plural signal line, an input line 34 for downloading the program instruction set or other information from an external computer, and an output line 36 which may communicate stored information to an external computer or data collector (not shown).

Controller 12 includes a CPU, or microprocessor 40 communicating along path 44 with memory 46 (which may include an external memory described hereinafter in this exemplary embodiment, or may be limited to internal CPU 40 memory), a low voltage power supply 48, and a digital input/output function 50, an A/D converter 52, and a UART 54 for communicating with an external computer, not shown. The power supply 48 includes a battery power source 56, a voltage splitter, and voltage regulator(s) as shown in FIG. 2, supplying operating voltage(s) at 58 and a battery voltage level signal at 60. The digital I/O 50 communicates along path 62, which may comprise a bus of, for example, 16 lines, the A/D path 64 may comprise a bus of, for example, 8 lines. The UART 54 or CPU 40 bus 54 need be only two lines.

A portable power supply 48 provides power to the vigilance monitor system 10 of the present invention. Power supply 48 includes a power source 56 which may be a battery pack or other source of direct current and a voltage splitter/voltage regulator 68 to provide the DC output voltage 58 for the regulator(s) voltage needed by the vigilance monitor system. Among the ambient and activity sensors 14 are a motion sensor 42 coupled to the subject by a path here identified as 20, which path may be mechanical or physical rather than electrical in nature. Ambient sound level is measured by ambient sound sensor 70. Ambient temperature is sensed by temperature sensor 72. Ambient light level is sensed by ambient light level sensor 75. The motion sensor signal, sound level sensor signal, temperature sensor signal, and light level sensor signals are analog signal levels in this illustrative embodiment; they are communicated to an analog-to-digital (A/D) converter 52 and communicated to the microprocessor 40 as digital signals along signal path 64. Of course, digital sensors may be substituted bypassing the A/D converter. The subject 16, is to be exposed to repeated stimuli in the course of operation of the vigilance monitor system 10 according to this invention.

For the purposes of this example only, the present invention contemplates aural and visual stimulation. Optional sensory touch stimulation may also be used, as is described hereinafter. For this purpose three light emitting diodes, identified as 74*a*, 74*b*, or 74*c*, or other light sources 74 are provided within the visual field of subject 16. Control of the LED lights 74*a*, 74*b*, and 74*c*, as well as control of the sound stimulator 76, is conveyed via one or more controller/stimulator signal lines 22.

Additionally, the sound stimulator (which may be a piezoelectric sound inducer) 76 is provided within audio reception range of the human subject 16. One or more generic signal paths 28 are provided for communicating aural and visual information from the stimulators 24. The LED lights 74 are provided within the visual path of subject 16; communication of the light along this visual path is represented in FIG. 2 by generic stimulation path 28. Similarly, the aural stimulation provided by piezoelectric sound inducer 76 communicates with subject 16; this path is also identified as generic path 28. Responses of subject 16 to the aural and visual stimulation provided by the piezoelectric sound inducer and lights are provided by one or more user pushbuttons 78 (78*a*, 78*b* in this illustrative example). The subject 16 presses one or more of the respective pushbuttons 78*a* or 78*b* in response to the presence of either light or sound stimulation; this is represented by response communication path 32. Feedback from the subject 16 to the controller 12 from the user pushbuttons 78*a*, 78*b* is via data response sensor/controller signal line 32.

Touch sensory stimulation may be provided by any of several devices known to those of ordinary skill in the art, including a silent "buzzer" acting as a vibrator, a heat or cold stimulator, an intermittently driven bimorph device, electrical current stimulation, or the equivalents thereof. Such devices may be included in the stimulators group 24 and communicated along generic path 28.

The stimulators 24 and the response sensor or sensors 26 communicate with the controller via an internal digital input/output circuit 50 which communicates directly with the CPU/microprocessor 40 on input/output lines 62. A data storage (memory) device 46 is included for storing the time data, ambient sensed signal data, and user response interval data to the various stimuli. The storage unit 46 can include memory, which, for example may be static random access memory or "flash" memory, their equivalents, or any of the above in combination with conventional magnetic storage such as a small portable disk drive unit. In the present embodiment, flash memory is used; 128K of "flash memory" SRAM is provided. Communication between the microprocessor 40 and memory/storage 46 is provided by memory line 44.

To facilitate input and output of data between an external computer (not shown) and the microprocessor 40 along data input and output lines 34 and 36, a conventional universal asynchronous receiver/transmitter (UART) chip is used. Internal communication between the microprocessor and the UART 54 is accomplished on lines 66.

Many of the controller functions are provided in this illustrative example by a small data logger engine 100 designed for portable data logging operations. A Model 5F Tattle-Tale data logger, commercially available from Onset Computer Corporation, North Falmouth, Mass., has been employed.

The Tattle-Tale 5F data logger 100 includes a small motherboard including an 8-bit microprocessor 40, such as an Hitachi 6303Y CPU. The 6303Y microprocessor is a CMOS CPU. It uses a superset of the Motorola Series 6800 instruction set, and it includes an on-board UART 54. The small motherboard also includes drivers for RS-232 Input/Output for digital I/O 50, an analog-to-digital A/D converter (LTC-1250) 52, at least one 5-volt voltage regulator 102, and a 9.8 MHz on-board crystal frequency source.

Figure 3:
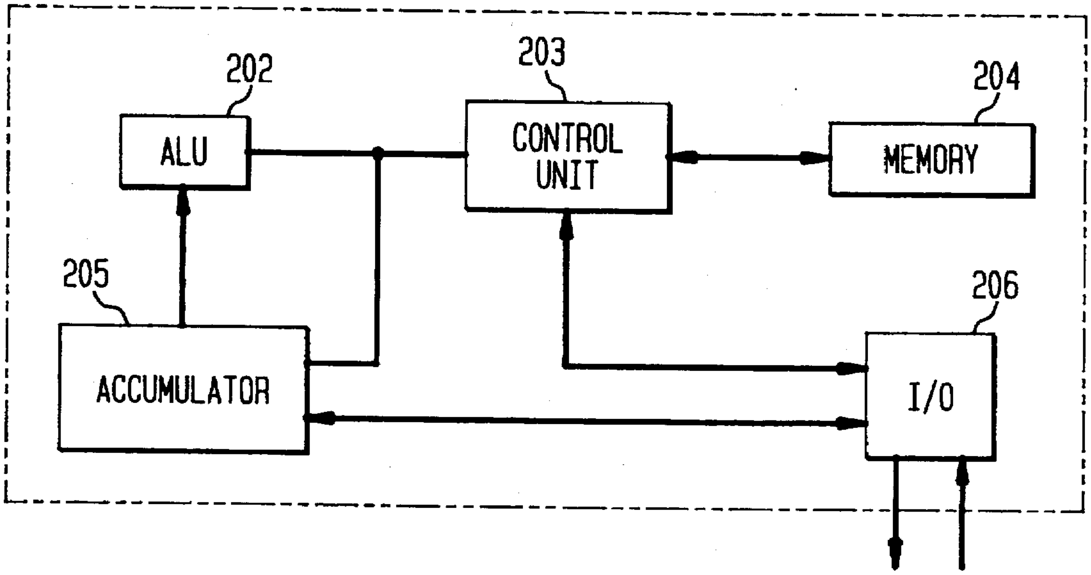
FIG. 3 is a simplified diagram of the computer of FIG. 2.

The CPU (microprocessor 40) is illustrated in greater detail in FIG. 3. As shown therein, the CPU 40 is of conventional design, and includes an Arithmetic Logic Unit (ALU) 202, a control unit 203 communicating with the ALU 202, and with a dedicated Input/Output (I/O) unit 206. ALU 202 performs logical operations such as AND, OR, etc., and arithmetic operations such as addition, subtraction, multiplication, and division. A memory unit 204 communicates with control unit 203 for temporary storage. The control unit 203 directs operation of the computer from the stored memory 204 instructions and executes these instructions. An accumulator 205 communicating with the ALU 202, control unit 203, and I/O unit 206 may be included for additional temporary storage of data. The I/O unit 206 handles the input and output operations, sending and receiving signals to and from the CPU 40.

The present exemplary embodiment includes two interconnected boards: the tattletale 5F serving as a motherboard, and a daughterboard to which generally are mounted and connected the power supply, sensors, signal conditioning, audible signalling, and the response pushbuttons.

The CPU in controller 12, operates under control of a program instruction set 110 all or part of which may be retained in the computer internal memory unit 204 during operation.

Figure 4:
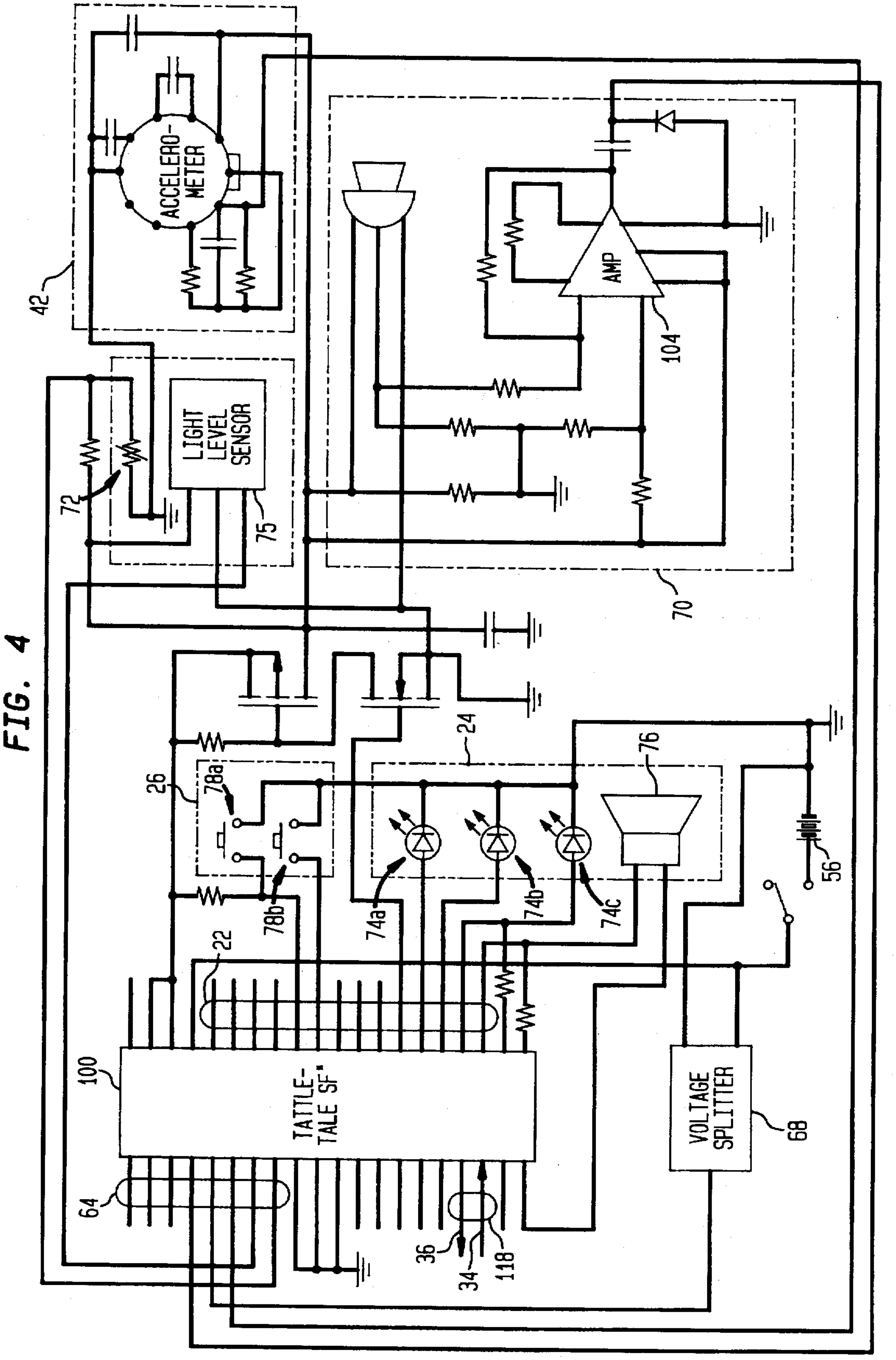
FIG. 4 is a detailed schematic diagram of the system of FIG. 1.

A complete schematic illustrating an exemplary embodiment of the invention is shown in FIG. 4. Referring now to FIGS. 1–4, the activity monitor system 10 is shown in detail.

In the present illustrative example, 128K of SRAM flash memory 46 is provided on the Tattle-Tale 5F motherboard. The small Tattle-Tale 5F motherboard and daughterboard also incorporates a voltage splitter device/voltage regulator (s) 68 which enables one of the A/D channels to monitor the battery charge condition, facilitating low battery power condition detection and shut-down of the system to thereafter conserve remaining battery power for memory retention. A Texas Instruments TLE 2426 chip is used for the voltage splitter/voltage regulator(s) 68.

An accelerometer 42 is located on the motherboard as an activity sensor. An Analog Devices, Inc., Model ADXL 50 g semiconductor accelerometer device having internal signal conditioning circuitry was selected for this illustrative example. Additional resistor and computer components have been selected to provide an adjustment of the accelerometer sensitivity to 10 g and to provide a DC output signal voltage to the A/D converter 52.

Lights 74*a*, 74*b*, and 74*c* are mounted to extend from the motherboard and project through a lightweight housing or cover protecting the vigilance monitor system 10. For example but not a limitation, the LEDs 74*a*, 74*b*, and 74*c* may be colored green, yellow, and red; other colors and color combinations can also be selected, or they may be all of the same color and merely symbolically coded, as by numbers, letters, or other characters or symbols. Standard T-¾ size LEDs were selected for the present example; however, other LEDs, including very low power LEDs may be selected. Other visual displays may be used, including alphanumeric and LCD screens.

Ambient sound detected by microphone 70, which also extends through the housing, is amplified by a small amplifier 104 connected to the motherboard. An instrumentation amplifier was selected in this example; however, an appropriate OP AMP, or other small amplifier may be used. The associated R/C components are used to set the gain and for signal conditioning. The directional characteristics of the sound level sensor 70 are affected by the location of the microphone on the housing and can also be affected by the housing design.

The Tattle-Tale 5F motherboard includes two voltage regulators; a first is used for powering all sensors and the microprocessor 12 functions, while the second is used by the digital logic circuits. Since the separate functions do not form a part of the claimed invention, they are shown as a single unit 68 and identified by a single regulated voltage output at 58.

Sound inducer 76 is electrically connected to the Tattle-Tale motherboard. A conventional piezoelectric speaker is used in this illustrative embodiment. In addition to, or substitution thereof, a vibrator such as a bimorph or DC motor vibrator such as the Namiki Precision of America PIN 6CE-150\WL may be used.

Figure 5:
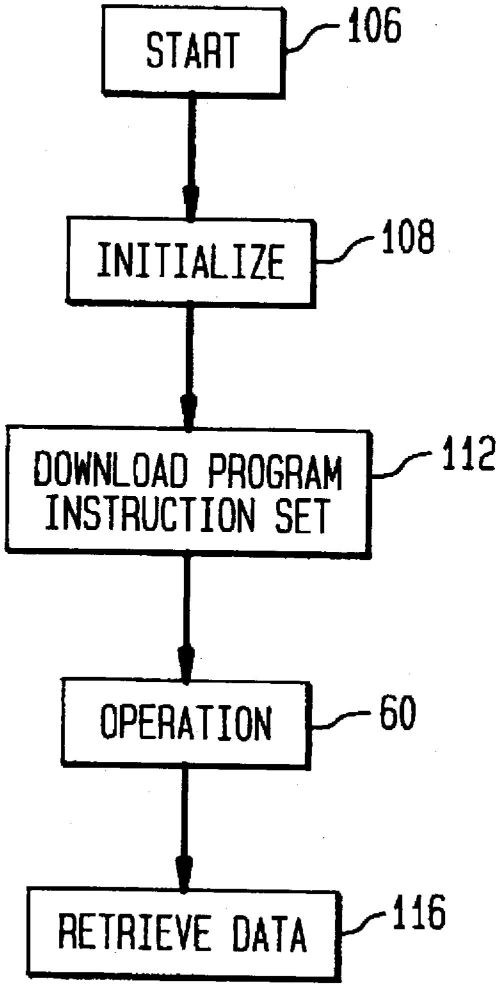
FIG. 5 is a simplified functional diagram illustrating operation of the system of FIG. 1.

A simple operating diagram is shown in FIG. 5. The vigilance monitor 10 is prepared for use at start block 106 by performing such maintenance operations as may be necessary to insure proper operation, including testing/replacing the battery 56. The monitor 10 is then initialized at Block 108 which may include resetting registers and clearing memory 46. This step is described in greater detail in connection with FIG. 13. Next, the program instructions set 110 is downloaded at Block 112 and operation begins when use of monitor is recognized, Block 60. Details and flowcharts of the operation are described hereinafter. When the desired operation is completed, the data stored in memory 46 may be retrieved at Block 116.

The vigilance monitor is operable in at least seven distinct modes. Each mode is illustrated generally by one or more the flowcharts (FIGS. 6–12) to be read in combination with a series of further detailed flowcharts (FIGS. 13–21).

Figure 6:
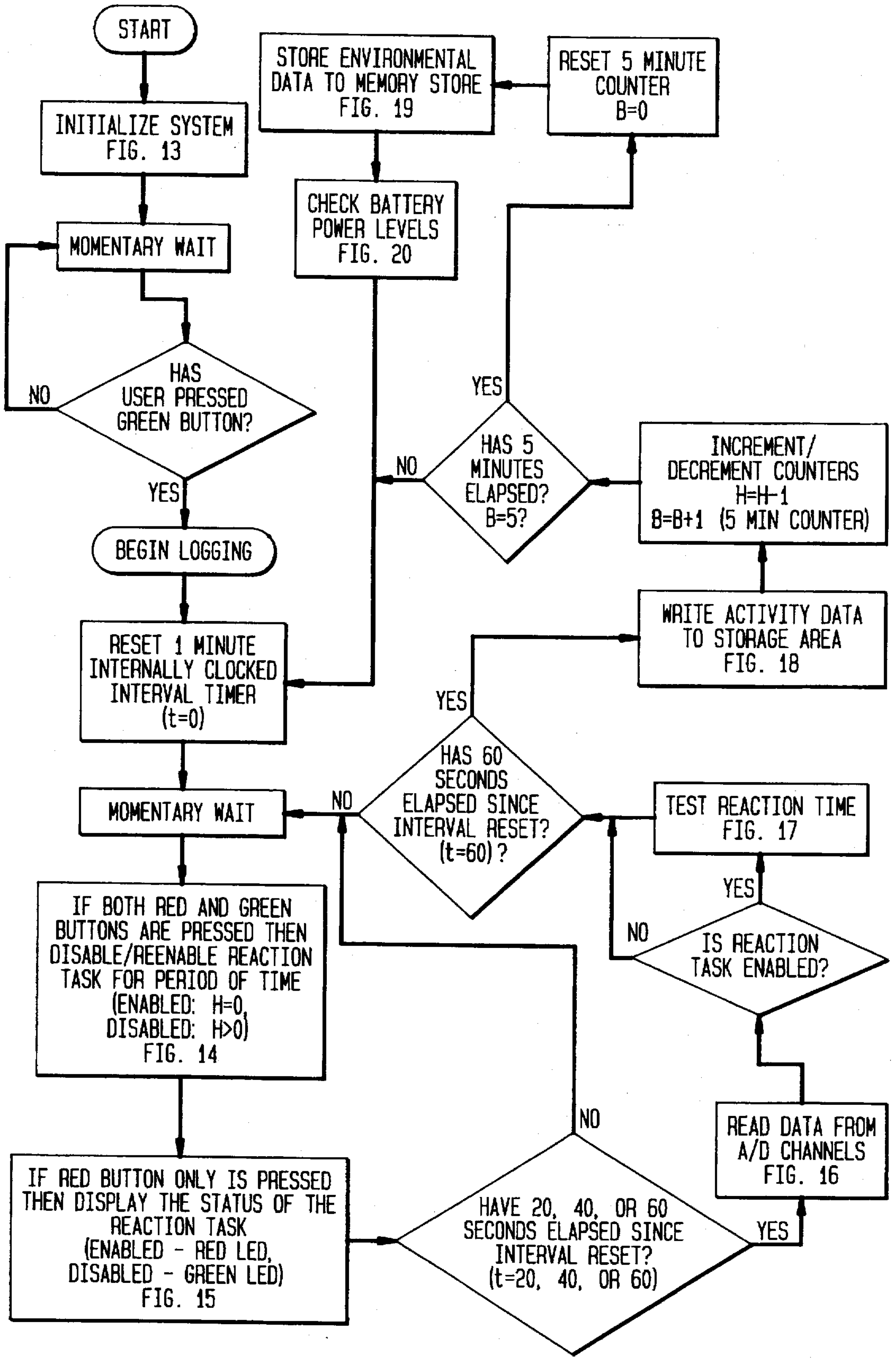
FIGS. 6–12 are flowcharts which illustrate the operating modes of the vigilance monitor.

The Random Timing-Reaction Task Mode is illustrated in FIG. 6, and is used in combination with the functions and procedural steps of several of FIGS. 13–20 as further identified hereinafter.

The purpose of this task mode is to continuously monitor physical activities of the subject, environmental variables, and subject reaction time responses at random intervals. Temperature, sound intensity, light levels, and other environmental factors are measured in five minute (or other defined) increments. The system monitors accelerations at (for example) three amplitude/frequencies in one minute (or other defined) increments, and randomly (for example, at an average of about once every fifteen minutes or at another interval set by the program instruction set 110) tests the reaction time of the subject 16.

The program instruction set 110 operation control begins by initialization (FIG. 13) which includes resetting memory and the program variables. Information including subject name, date, and time is requested from and stored to a separate header section of the data storage area in memory 46.

Figure 14:
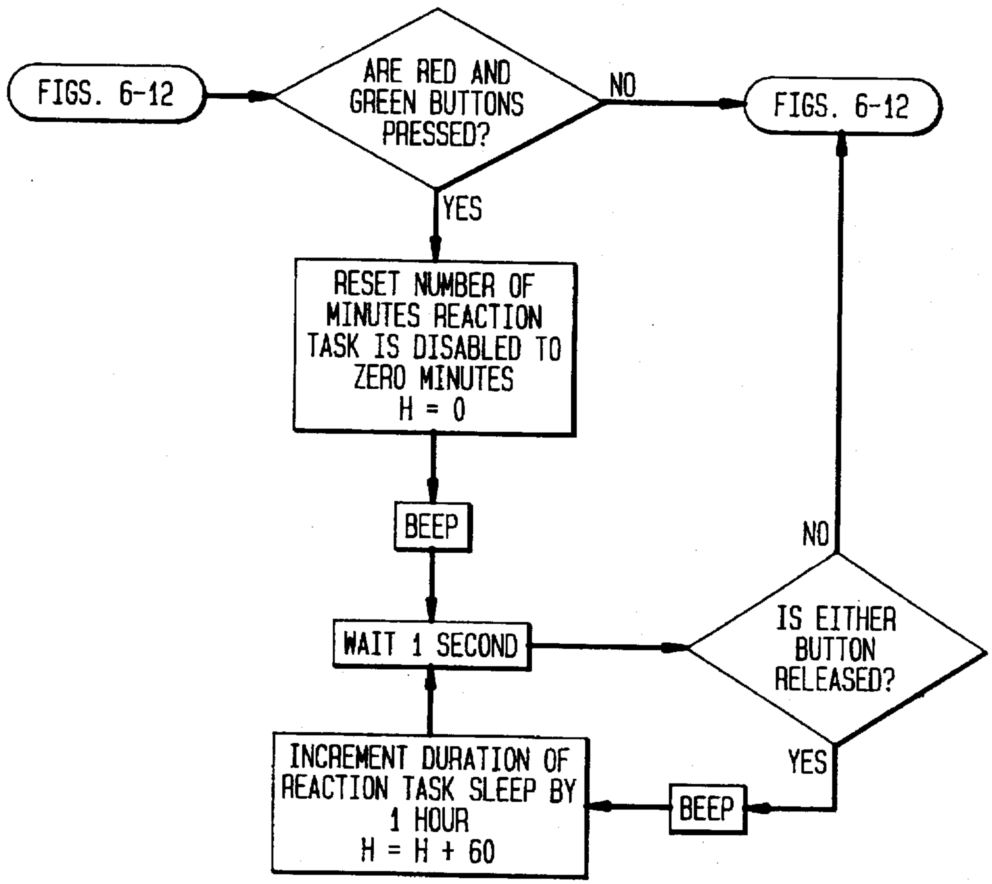
Figure 15:
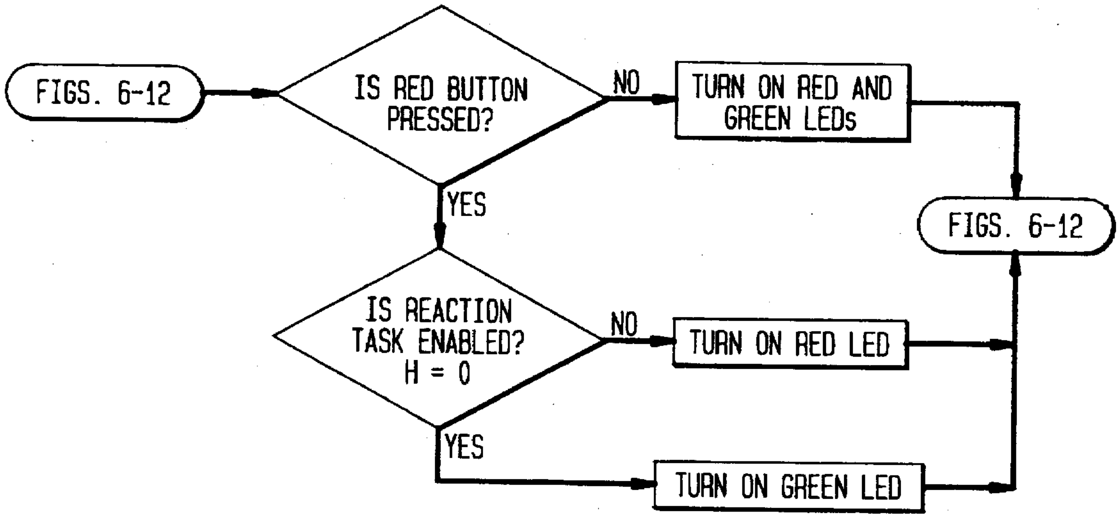

Once the program instruction set 110 has begun running, the subject 16 is required to respond periodically to a stimulus such as an audible tone by pressing either of the pushbuttons. The audible alarm 76 can, if desired, be disabled temporarily, for example, by pressing and holding both pushbuttons 78*a*, 78*b* simultaneously (FIG. 14). Pressing one of the pushbuttons, for example the red pushbutton 78*b* only will light either a red LED 74*c* indicating that the reaction task is disabled, or a green LED 74*a* indicating that the reaction task is enabled, thus indicating Reaction Task Enabled/Disabled status (FIG. 15).

Figure 16:
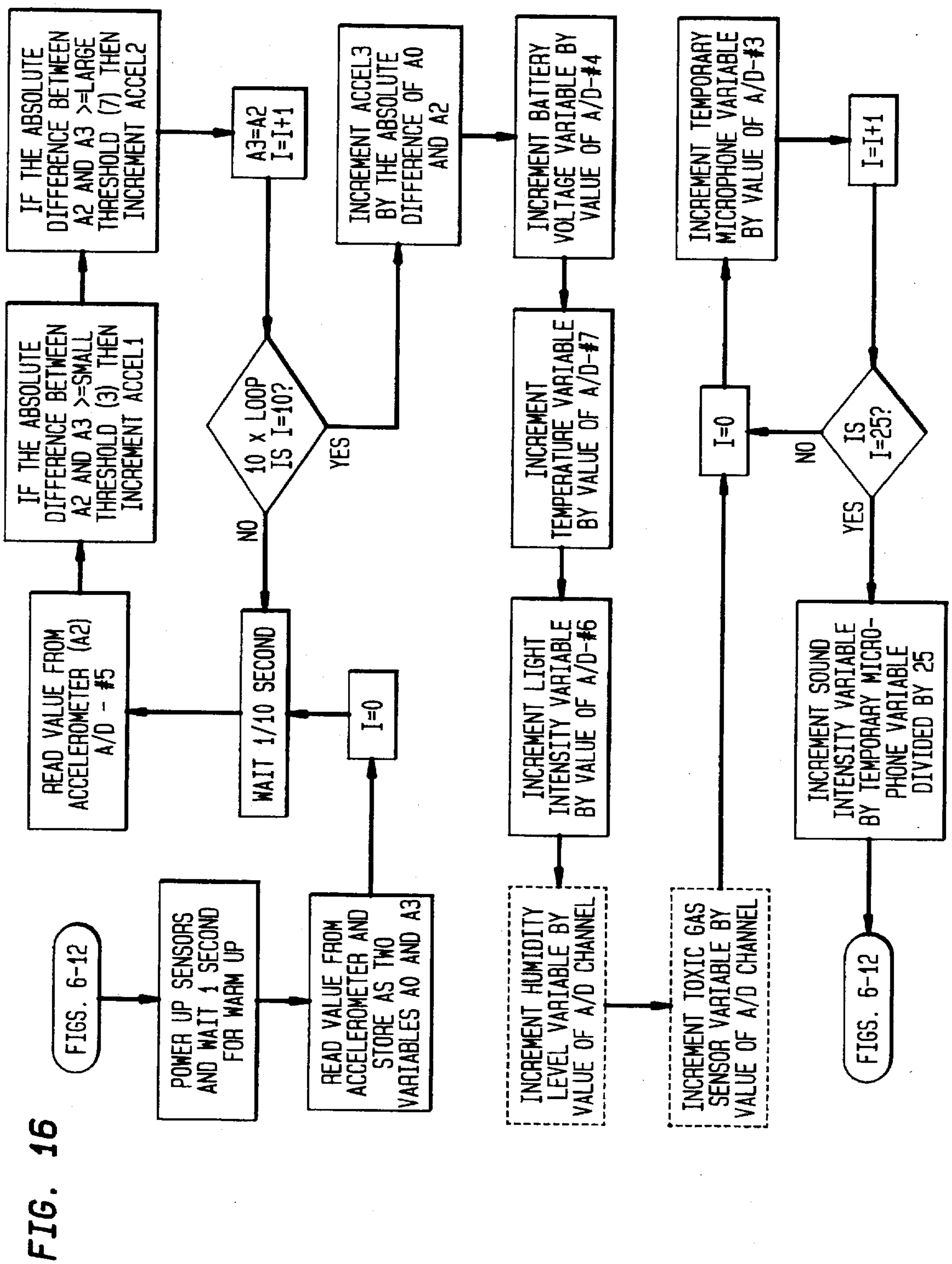
Figure 20:
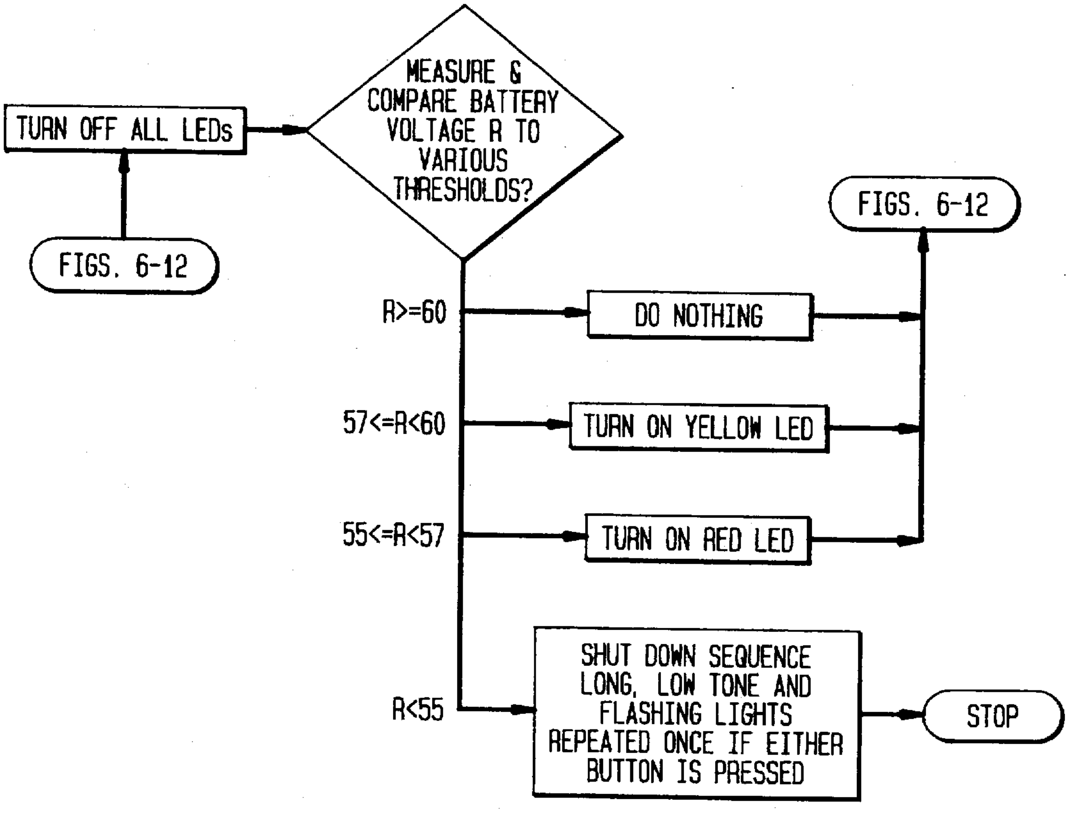

During program instruction set controlled operation, the analog-to-digital channels 64 are sampled (in this example) at intervals of about every 20 seconds (FIG. 16). Data from the accelerometer 42 is summed in three storage areas or "bins" of different amplitude/frequencies and this data is then written to the memory 46 data store periodically (FIG. 18), for this example, once every minute. Data from the environmental sensors 14 is averaged over a period of time, for example, 5 minutes, and then is written to the data file at that time (FIG. 14). Periodically, the program instruction set examines the data from the voltage splitter 68 to verify that sufficient battery 56 power exists for continued operation (FIG. 20). As the voltage decreases to a predetermined level, a warning is given. For example, the yellow 74*b* and/or red 74*c* LEDs may be activated. If the voltage reaches a sufficiently low level, the system 10 warns the subject as by an audible tone or other signal and then shuts down to preserve data stored in memory.

Figure 7:
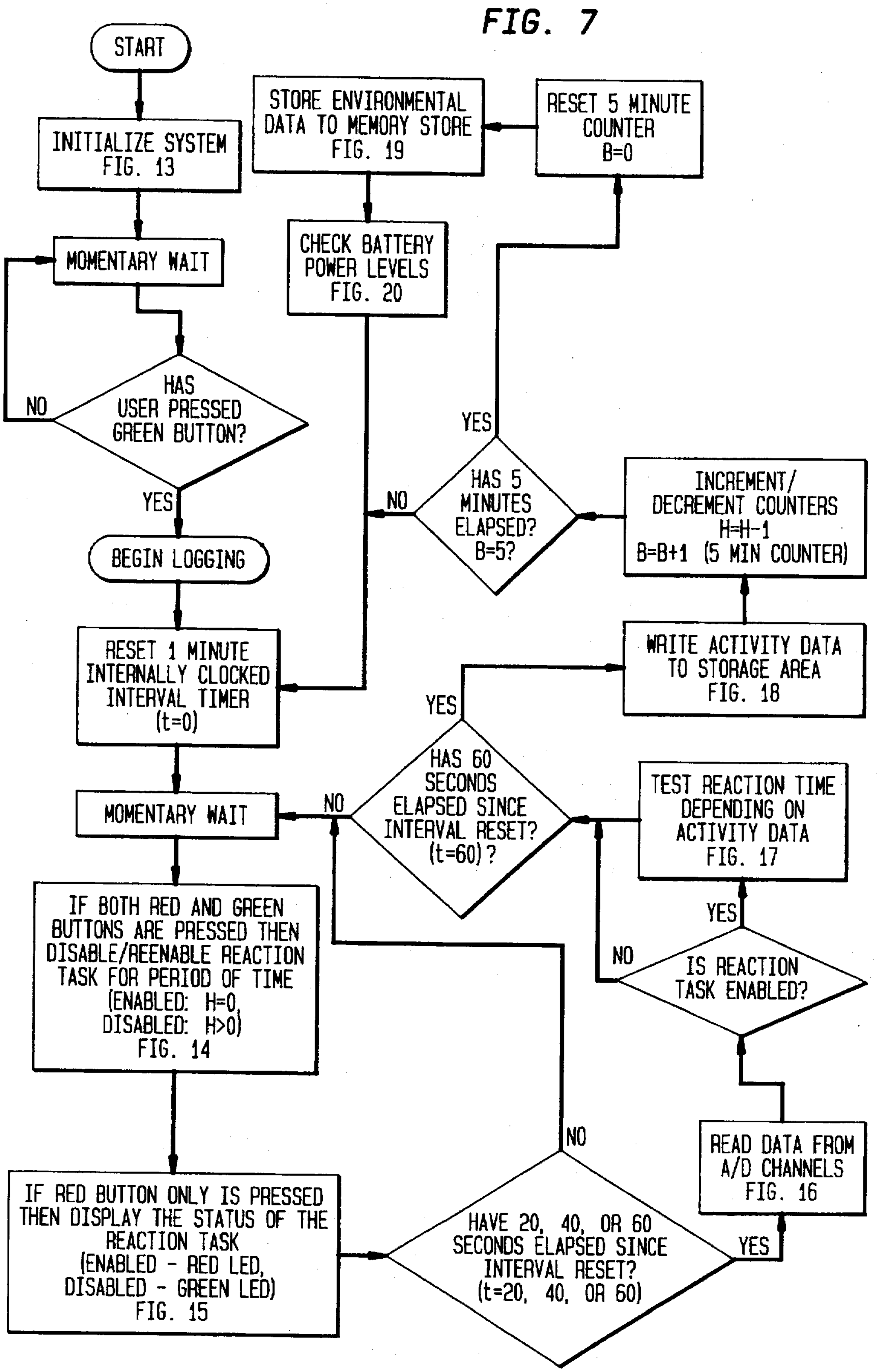

The Active Evaluation—Reaction Task Mode is illustrated in FIG. 7, and is used in combination with the functions and procedural steps of several of FIGS. 13–20 as further identified hereinafter.

The purpose of this task is to prevent sleepiness of the subject 16 by monitoring patterns of the subject's activity. If the patterns of activity indicate the subject may becoming drowsy, an alarm, which may, for example, be an audible alarm from speaker 76, is initiated; the alarm requires the wearer to respond, as by pressing a pushbutton.

The Active Evaluation—Reaction Task Mode is substantially identical to the Random Timing—Reaction Task Mode in operation except that the decision to signal an alarm is based on a stored history of activity data. The decision to signal the alarm is made on the basis of an algorithm that takes into account present and recent past activity levels. Once a reaction test is made, the device disables the reaction task for a period of time which may be predetermined or may be set by the algorithm.

Figure 8:
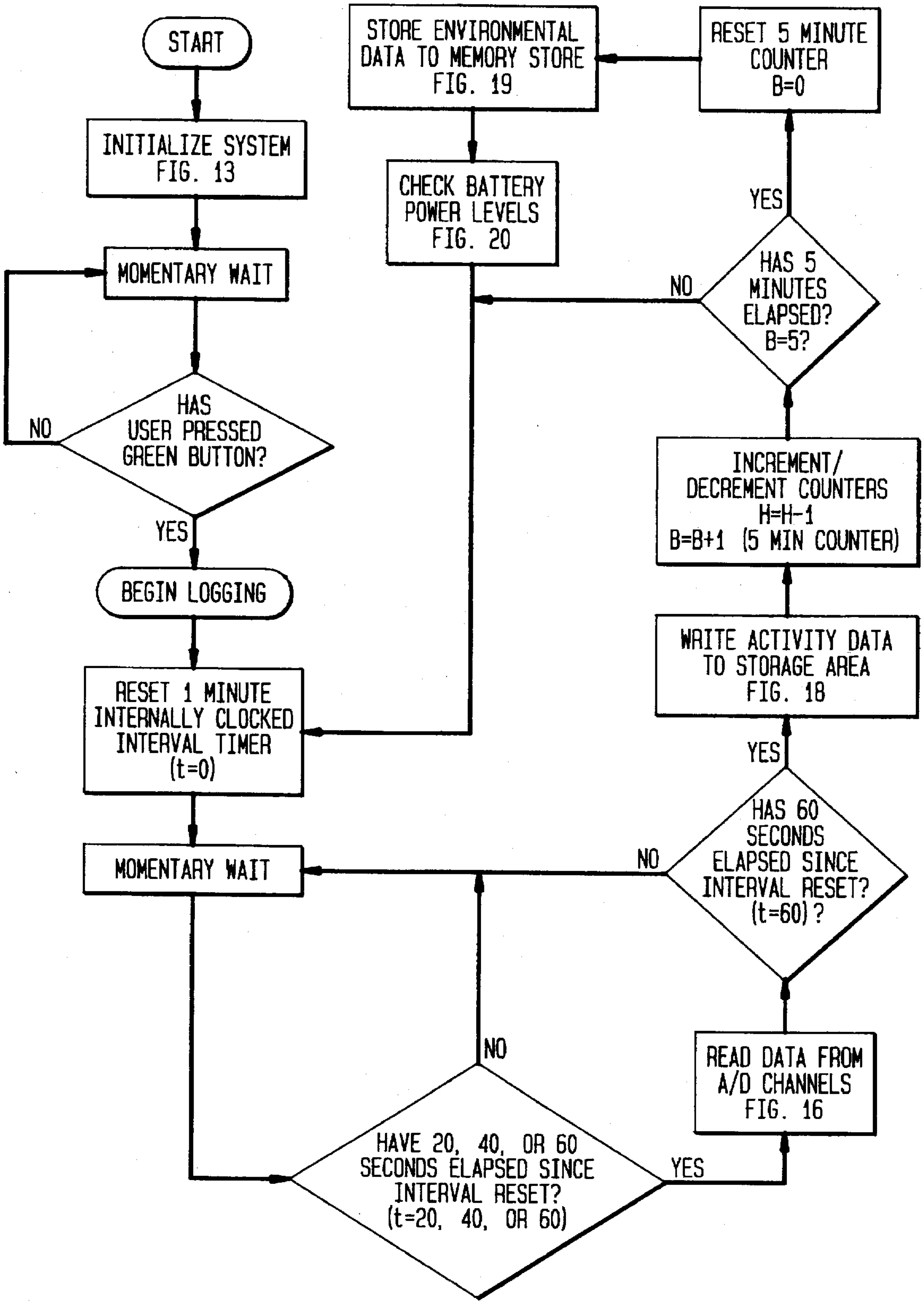

The No Reaction Task Mode is illustrated in FIG. 8, and is used in combination with the functions and procedural steps of several of FIGS. 13–20 as further identified hereinafter.

The implementation of this mode samples and records the subject's activity and several other environmental variables as may be desired. No alarm signal is used to alert the subject 16, or to monitor subject reaction time intervals. With respect to initialization (FIG. 13), data sampling (FIG. 16), and data storage (FIG. 18), operation under program instruction set 110 control is substantially identical to the Random Reaction Task Mode and the Active Evaluation Reaction Task discussed above.

Figure 9:
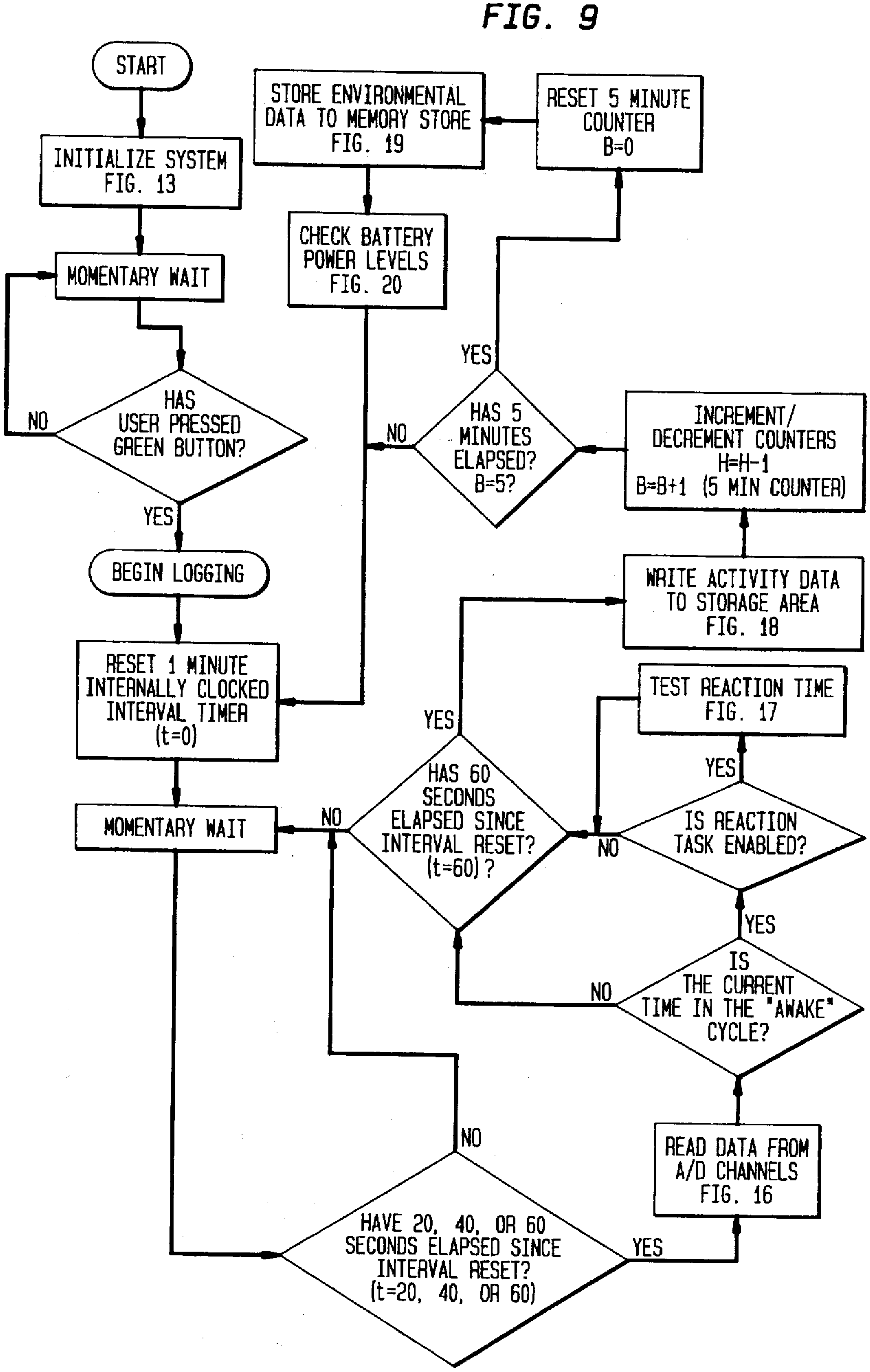

The Circadian Synchronization Mode is illustrated in FIG. 9, and is used in combination with the functions and procedural steps of several of FIGS. 13–20 as further identified hereinafter.

The Circadian Synchronization Mode uses the monitor system 10 to modify circadian rhythms by producing a change in the behavior patterns of the subject 16 by actively modifying rest-activity patterns and subject vigilance. The program instruction set operation is nearly identical to either the Random Timing—Reaction Task Mode and the Active Evaluation—Reaction Task Mode, except that an extra conditional step is required. The Reaction Time Test (FIG. 17) is only permitted to occur between specified hours. Any of the usual alertness modes can be used to prevent sleepiness and sleep (random timing, active evaluation) onset. It is possible for the program to be set such that the subject 16 can temporarily disable the alarm (FIG. 14).

Figure 10:
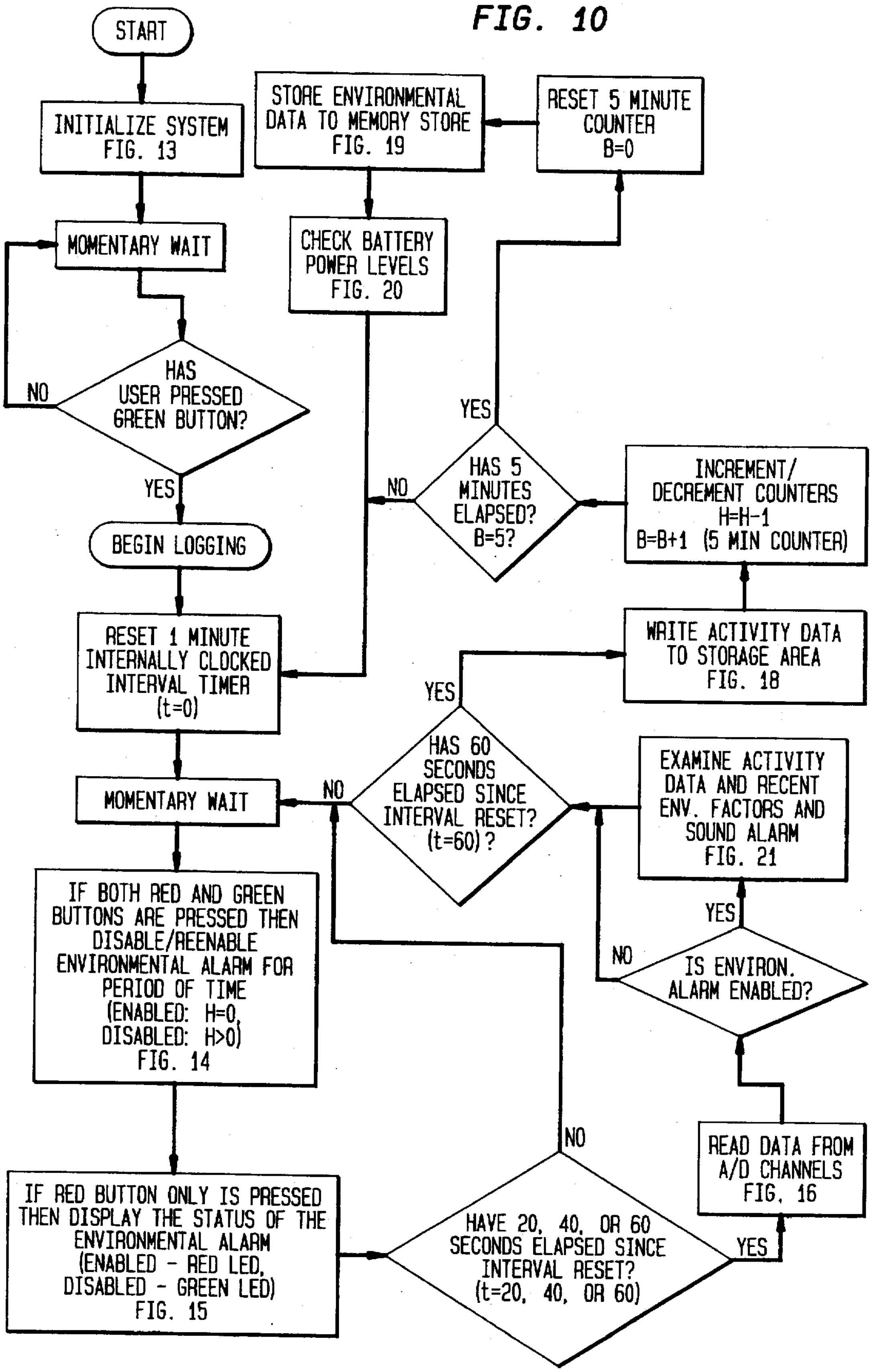

The Environmental Stress Mode is illustrated in FIG. 10, and is used in combination with the functions and procedural steps of several of FIGS. 13–21 as further identified hereinafter. The Environmental Stress Alarm Mode is included to provide a warning signal to the subject 16 of certain potentially hazardous situations. If one or more activity or environmental sensed factors meet predetermined criteria (FIG. 21), then an alarm signal (which may be audible from sound stimulator 76) will be triggered to warn the subject. Examples of potentially stressful or hazardous situations that the device can be configured to monitor include: Lack of sensed movement, low sensed activity levels combined with low sensed environmental temperatures, high sensed activity levels combined with high sensed environmental temperatures, high sensed levels of toxic gases, moderate sensed levels of toxic gases combined with high sensed activity levels, sensed slowing reaction times combined with changes in sensed toxic gases, and/or sensed slowing reaction times combined with an increase in either sensed environmental temperature extreme.

Figure 11:
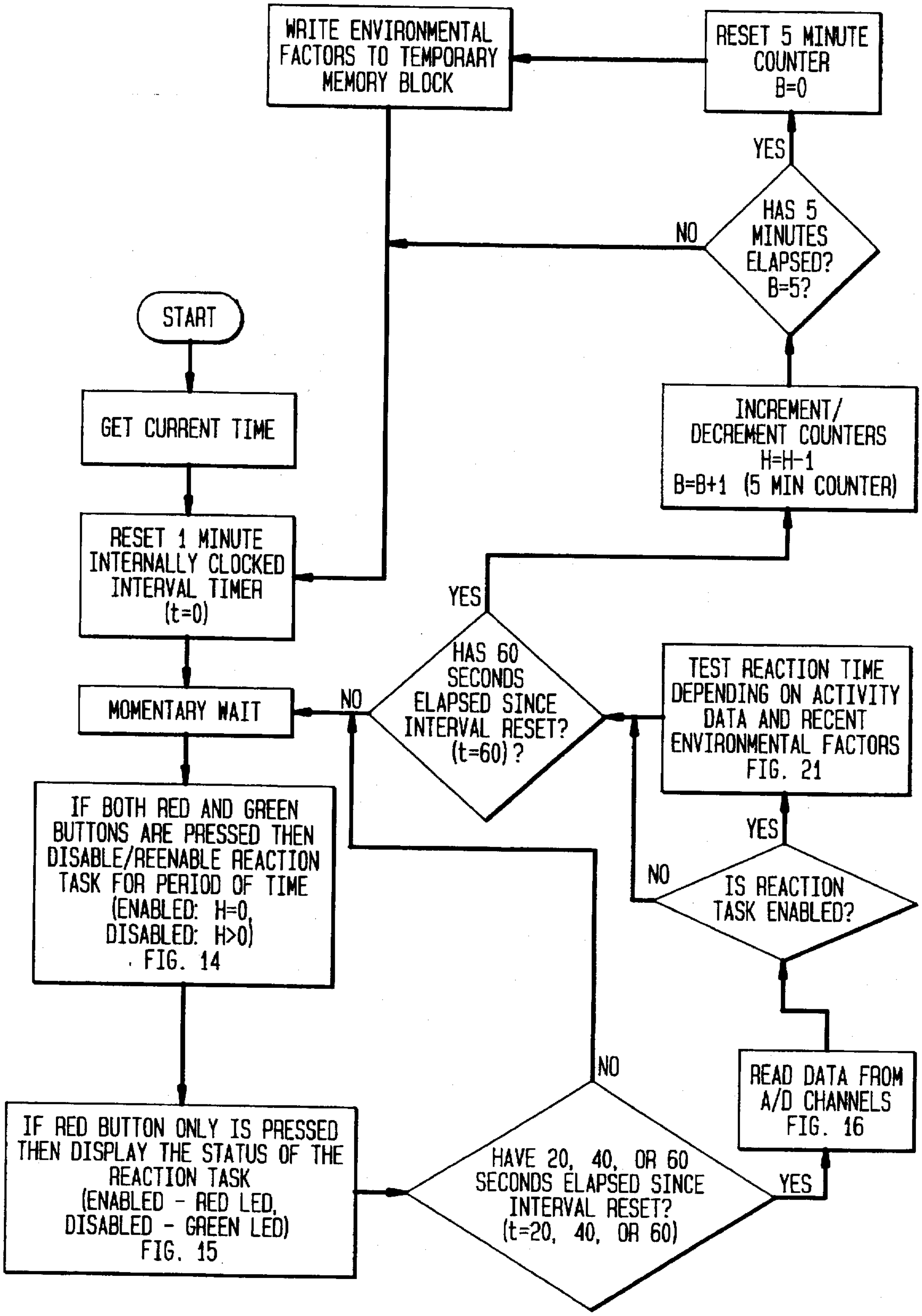

The Simple Alarm Mode is illustrated in FIG. 11, and is used in combination with the functions and procedural steps of several of FIGS. 14–21 as further identified hereinafter.

A simple alarm program is be used to sense and monitor any environmental or activity factor, and sound an alarm when a certain combination occurs. No data logging will occur. The only initialization would be for the current time.

Figure 12:
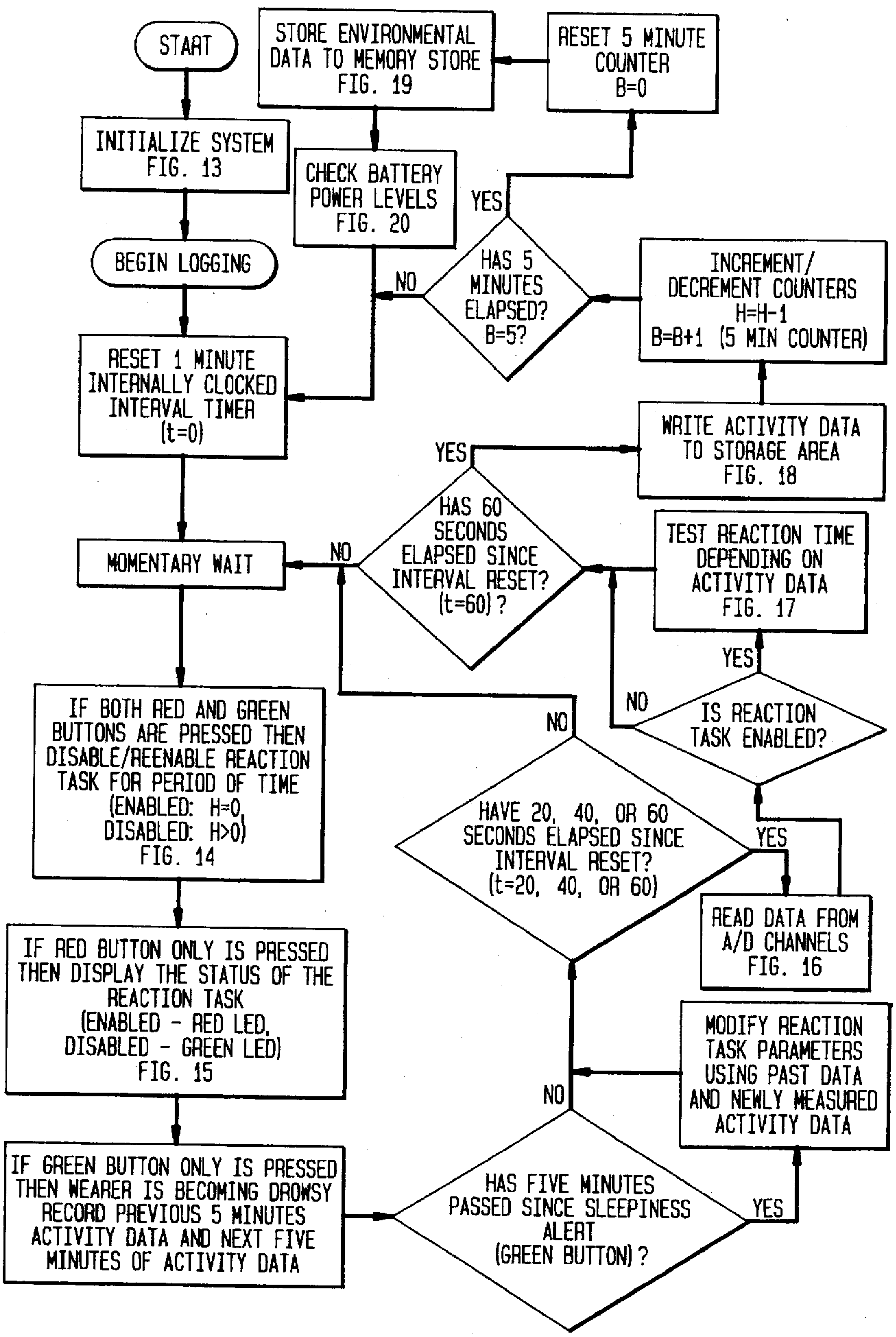

The Learning Mode is illustrated in FIG. 12 and is used in combination with the functions and procedural steps of several of FIGS. 14–21, as further identified hereinafter.

The purpose of this mode is to base the alarm task on self-reported periods of sleepiness. The subject 16 presses a pushbutton to notify the monitor 10 when a feeling of sleepiness occurs. This information is then recorded and stored, at, for example, 5 minute intervals. The monitor 10 will then use information recorded from the 5 minute periods before and after the user signal to modify the sensed activity alarm parameters using an algorithm. Once modified, the new parameter values are used to determine when the subject 16 is becoming sleepy and to sound an alarm.

Initialization and recording of sensed subject activity data and sensed environmental factors is substantially the same as the Active Evaluation Reaction Task Mode described above.

Figure 13:
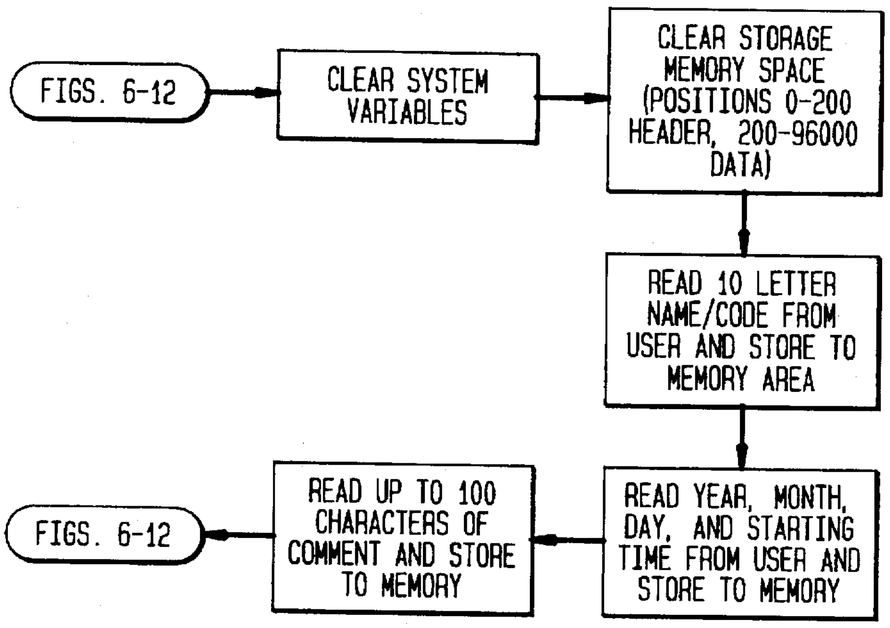
FIGS. 13–21 are flowcharts which illustrate specific functions and features associated with the FIGS. 6–12 flowcharts.

In operation in all seven normal modes described above, there is a first "START" step (Block 106 of FIG. 5), followed in all modes but the Simple Alarm Mode (FIG. 11) by an initialization step (Block 108, FIG. 5), FIG. 13.

The initialization step portion of the program instruction set 110 software sets most program variables to zero. Exceptions include a global time variable L, and the Reaction Task delay counter. The Reaction Task delay is preset in this example to prevent the alarm from being signalled prematurely. All Input/Output connections (I/O Bus 22) are set to zero (except certain connections which have hardware pull-downs) to prevent value drift.

The main data storage area in memory 46 is prepared for data storage. In this example, a 96K portion of the 128K SRAM is provided for data storage. The first 200 bytes of data are set to blank spaces to form a header area. The remainder of the data bytes are set to '#' to form the sensor logging area.

A momentary wait is needed so the processor is not continuously working while waiting for user to indicate "go". This momentary wait is not needed by either the Simple Alarm Mode (FIG. 11) or the Learning Mode (FIG. 12). Except in these two modes, the program instruction set 110 checks to see if the subject 16 has pressed the green pushbutton 78*a*. Refer to FIGS. 11 and 12. Logging of data occurs next in all modes except the Simple Alarm Mode, FIG. 11. The internal interval timer is to be reset periodically; one minute intervals are selected in this embodiment for all modes followed by a momentary wait. Refer to FIGS. 13–21.

The Reaction Task Modes can be disabled and re-enabled by pressing both pushbuttons 78*a*, 78*b*. Refer to FIG. 14. The Reaction Task function (or routine) (FIG. 17) is not used in the No Reaction Task Mode and the Circadian Synchronization Mode, FIGS. 7 and 8.

The Toggle Reaction Task (FIG. 15) portion of the program instruction set BL allows the subject 16 to temporarily disable the reaction task.

If both of the pushbuttons 78*a*, 78*c* are pressed and held briefly, the program instruction set 110 will set the period that the alarm is disabled to zero minutes. This is signaled to the subject 16 as by a distinctive alarm. Once every second that both pushbuttons remain pressed, the monitor 10 will beep once. Each beep indicates that the monitor 10 will be disabled for an additional 60 minutes or other predetermined time interval. There is no limit to the number of time intervals that the reaction task can be disabled.

The Reaction Task routine may also, if desired, include program instruction set 110 routines for displaying the status of the reaction task. Refer to FIG. 15.

The Display Status of Reaction Task (FIG. 15) portion of the program instruction set 110 can be used to provide a feedback to the subject 16. A dual function is then presented. Upon pressing and holding the red pushbutton 78*b*, the monitor 10 will light either a green LED light 74*a* indicating that the reaction task is enabled, or a red light 74*c* indicating that the reaction task has been disabled. If none of the LEDs lights 74*a*–74*c* is lighted, then the program instruction set BL has stopped running, likely because of either an automatic software shutdown, or due to a hardware failure.

Six of the seven modes require the environmental data to be collected and stored in memory 46 (FIG. 16). The exception is the Simple Alarm Mode illustrated in FIG. 11. The pushbutton power level check may also be omitted for this mode.

The Read Data from A/D Channels portion of the program instruction set 110 illustrated in FIG. 16 controls reading of all the data from the Analog to Digital channels on A/D bus 64. There is a short power up period for the sensors before data logging begins.

The ACCEL1 and ACCEL2 data shown in FIG. 16 are sampled, for this example, 10 times at 10 Hz. If any sample exceeds a threshold value, the value of ACCEL1 or ACCEL2 is incremented. ACCEL3 is sampled once at 0.1 Hz. The difference value is added to the ACCEL3 variable.

Battery voltage, temperature, light intensity, humidity level, and toxic gas levels (if sensed and used) are sampled once during the read cycle. The sound level sensor 70 is sampled 25 times and the average value of the samples is used as the sound intensity level.

A series of timing functions then follow (FIGS. 6–12). The first time increment is a test to check that 5 minutes has elapsed on a 5 minute counter and is related to the increment/decrement counter function. The second time increment is a test to check that 60 seconds has elapsed since the reaction time interval has been reset. In all modes except the Circadian Synchronization Mode, FIG. 9, the period since the interval has been reset=20, 40, or 60 seconds is checked (FIGS. 6–12).

Omitted from the Simple Alarm Mode (FIG. 11) are the steps of writing activity data and the Test Reaction time data to the storage area in memory 46. These may be utilized for all other modes (FIGS. 6–12).

Figure 17:
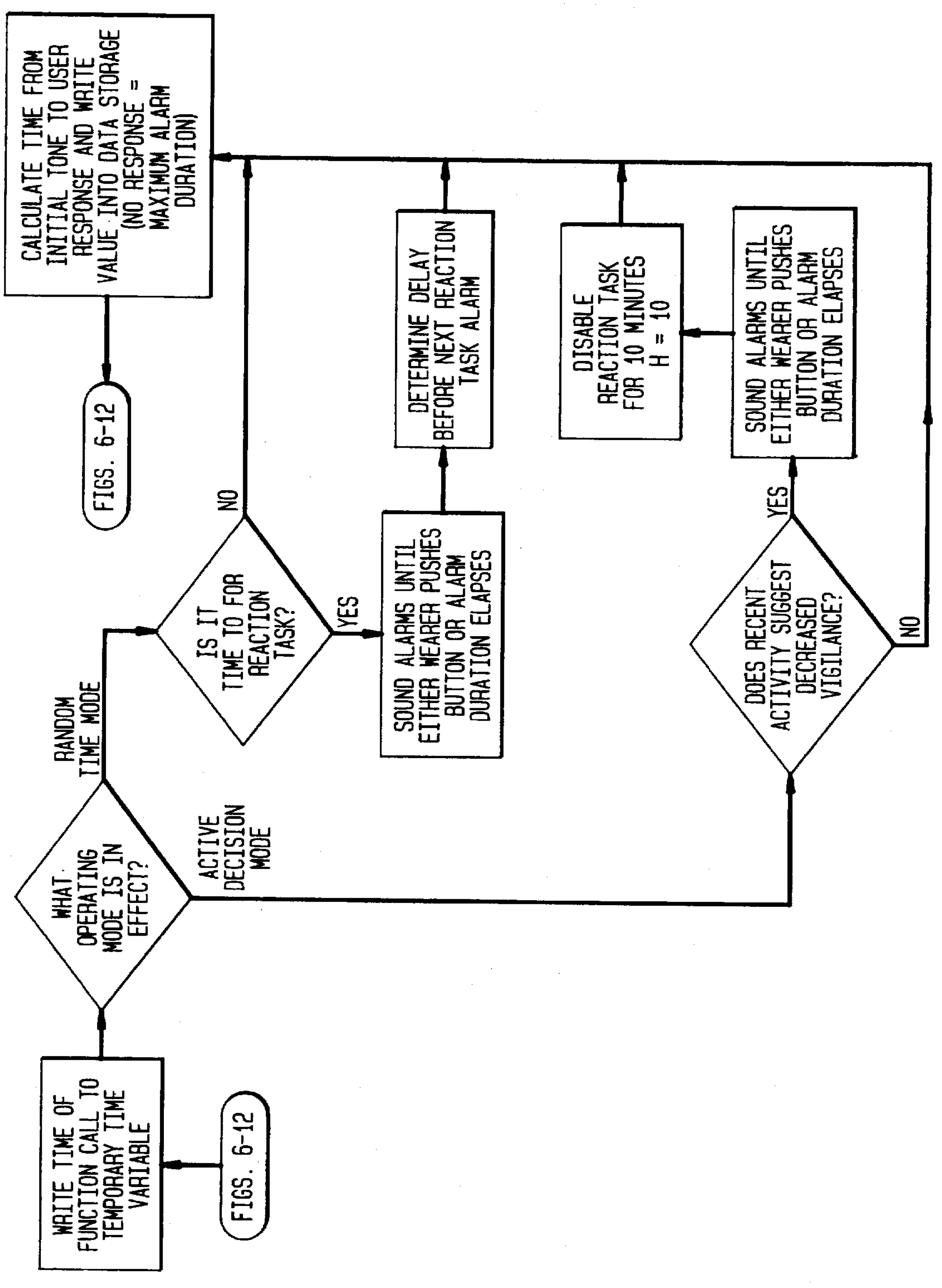

The Test Reaction Time function is shown in FIG. 17. The reaction time is not tested in the No Reaction Task Mode or in the Environmental Stress Mode (FIGS. 8 and 10), and is performed differently in the Simple Alarm Mode (see FIG. 11). In all other modes, the reaction test time operation is described in FIG. 17.

A portion of the program instruction set 110 is directed to testing the reaction subject's test reaction time. This portion of the program instruction set controls generation of an audible tone, then times the period of the response until the subject 16 presses a pushbutton 78*a* or 78*b*. Two different methods are used for determining when to signal an alarm in the exemplary embodiment of the present invention. In "random time" operating mode the monitor 10 is configured to randomly choose the number of minutes between alarms. An upper and a lower bound for the time duration are set as parameters in the program instruction set 110.

The "active decision" operating mode analyzes recent subject activity data to decide if the subject 16 has become less vigilant. If so, an alarm is signalled. After the alarm is signalled, the reaction task is disabled for 10 minutes.

The reaction task data is written to the data storage in the following format:

$AB where the "$" indicates that the following two characters should be interpreted as the reaction task times. In this example, the subject 16 took "A" seconds plus "B"/100 seconds to respond to the stimulus. Alarm stimuli, such as audible sounds, can be customized for each subject to prevent confusion if several subjects are present at the same time.

Figure 18:
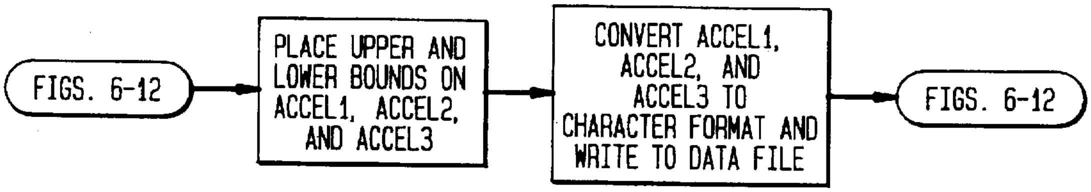
Figure 19:
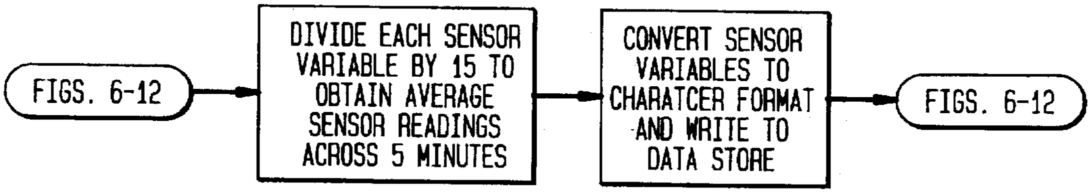

Activity data is written to storage as shown in FIG. 18 in all modes except the Test Reaction Time Mode, FIG. 11.

The program instruction set 110 writes three channels of activity data to the data storage file. The three channels of data represent:

ACCEL1—high frequency 10 Hz—low amplitude movements

ACCEL2—high frequency 10 Hz—high amplitude movements

ACCEL3—low frequency 0.1 Hz movements

See also Read data from A/D Channels (FIG. 16) above for more details.

Each activity channel is bounded as follows in this example:

$0<ACCEL1<200$

0<ACCEL2<200

0<ACCEL3<20000

Sensed activity data is converted to ASCII, so that ACCEL1 and ACCEL2 can be represented by a single byte and ACCEL3 is represented by only two bytes. These four bytes are then written to the data storage area of memory 46.

Environmental data is stored periodically in all modes (FIGS. 6–10, 12) except Simple Alarm Mode, FIG. 11. In Write Environmental Data to Storage (FIG. 19), environmental data is stored. At every five minute operating interval, the program will write the average reading from the various environmental sensors 14 to the data storage area 46.

To obtain an average, each sensor variable is divided by 15 since each sensor is sampled three times/minute for five minutes. The resulting data is converted to ASCII format and stored to the data storage area of memory 46 in the following format:

!KKNTT where "!" is a single byte that indicates that the subsequent section of data represents the environmental data readings. "KK" represents two bytes of data which encode the sound intensity levels sensed at sound sensor 70. "N" is a single byte representing the sensed light intensity level at light sensor 75. "TT" is a two byte word representing the average sensed temperature from temperature sensor 72 in degrees Celsius. Additional sensors such as humidity or toxic gas sensors (FIG. 16) are similarly encoded into the data file.

Check Battery Power Levels is illustrated in FIG. 20. The program instruction set 110 includes a routine to test and indicate the battery 56 power levels to the subject 16, and if necessary to shut down operation of the monitor 10 to preserve all measurement data that has been stored in memory 46.

Initially, all LEDs **74*a*–74*c* are powered down to clear possible inputs from different modules. The value supplied to the A/D bus 64 input corresponding to the voltage splitter/sensor 68 is then checked to determine if the shut down mode action of the software is necessary. If the battery 56 power measured by splitter 68 is of sufficient strength, the program instruction set 110 continues normal operation. As the battery voltage decays (signaling an imminent power shortage), either the yellow or red LED 74*b* or 74*c* (or both) is lighted continuously to alert the subject 16. Once the battery 56 voltage level has fallen to a predetermined threshold point, the monitor 10 goes into an automatic shutdown mode (FIG. 20) procedure to preserve the data stored in memory 46. The shutdown sequence can, for example, consist of a series of low frequency, long duration signalling tones. The monitor then only checks the state of the pushbuttons. If either pushbutton is depressed, the low power alarm sequence is repeated once again and the monitor completely terminates operation of the program instruction set 110**.

Figure 21:
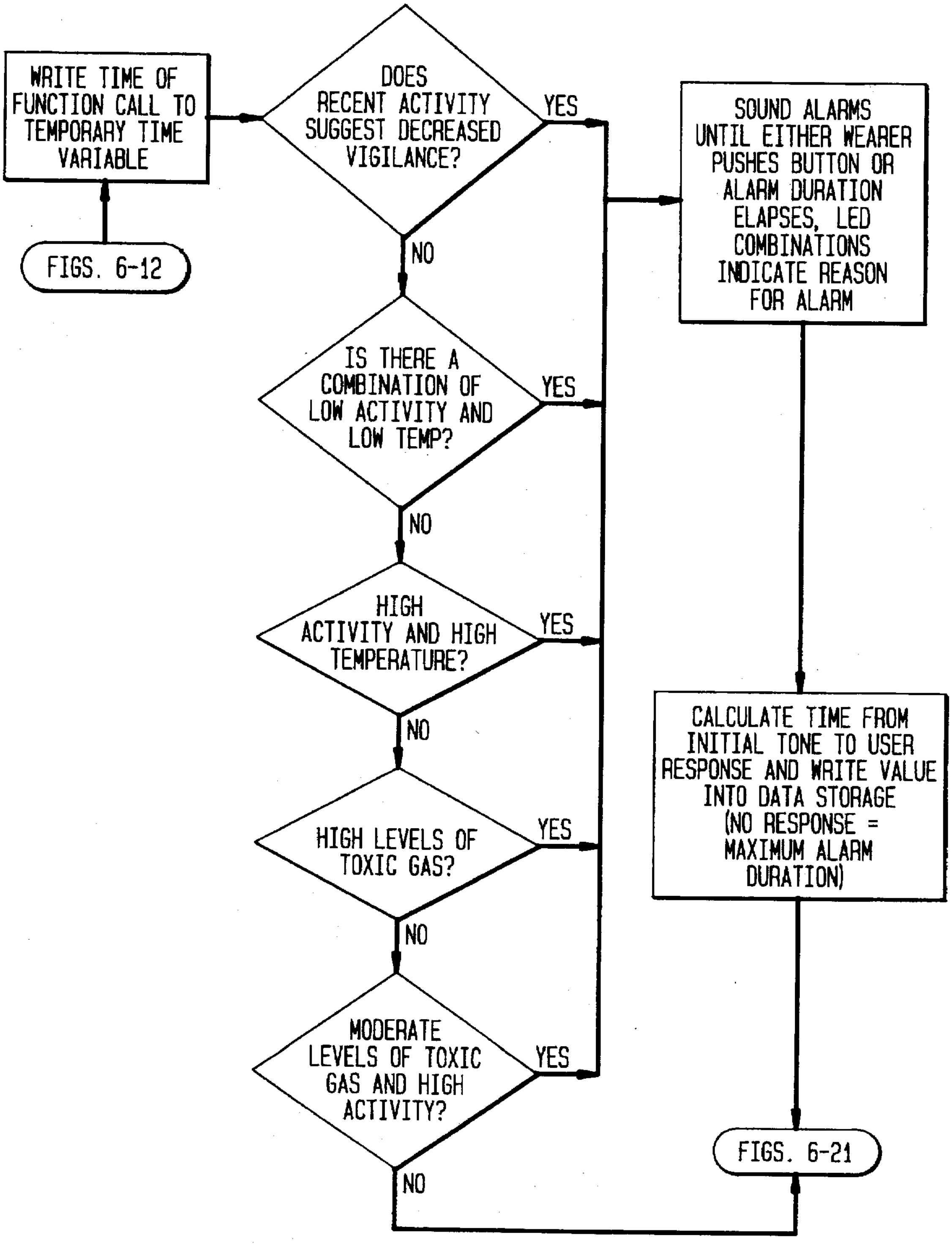

The Examine Environmental Factors routine is illustrated in FIG. 21. This portion of the program instruction set 110 is configured to examine several sensed environmental factors and sensed subject 16 activity levels to warn the subject of potentially hazardous environmental situations. When such an environmental situation is encountered, the monitor 10 sound stimulator 76 will signal the alarm. Different combinations of LEDs **74*a*–74*c* can also be used to indicate the potential problem without an audible alarm. The alarm can be signalled once every measurement cycle until either the hazardous situation is terminated or until the subject 16** disables the alarm for a period of time.

Some typical examples of potentially stressful or hazardous situations that the system 10 can monitor include:

Lack of sensed movement of subject 16

Low sensed subject activity levels combined with low sensed environmental temperatures High sensed subject activity levels combined with high sensed environmental temperatures High levels of toxic gases sensed (FIG. 16)

Moderate levels of sensed toxic gases sensed in combination with high sensed subject activity levels Sensed slowing subject reaction times (FIGS. 6–7) combined with changes in sensed toxic gases or temperature extremes.

It is contemplated that the reaction task can be modified to also evaluate performance and/or memory abilities of the wearer. Either at preset times of the day, or when activity and reaction time tests indicate an increase in sleepiness, simple or complex mental, or psychomotor tests can be presented to the wearer. Such tasks can be configured to be of either short or long duration. Some examples of possible tasks are:

Requiring the subject to distinguish between different frequency tones by pressing either the red or green pushbutton.

Requiring the subject to distinguish between long or short tones.

Requiring the subject to press different pushbuttons depending on LED color combinations displayed.

Requiring the subject to respond when a short sequence of LED light flashes is repeated during a long sequence of flashes.

Requiring the subject to respond when either a frequency or tone duration matches a LED light flash.

Requiring the subject to recall a short sequence of red and green LED light flashes by pressing the red and green pushbuttons in the correct sequence either after no delay, or after a short delay. The number of events in the sequence can be gradually increased.

Based on substandard performance a warning alarm can be provided.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

I claim:

1. A human subject vigilance monitor, comprising:

a) a plurality of ambient environmental sensors, each adapted to produce an output signal;

b) at least one source of human subject stimuli;

c) at least one human subject response sensor, each adapted to produce an output related to subject initiated responses to the stimuli;

d) a controller having a CPU, a digital I/O communications circuit communicating with the CPU, an A/D converter communicating with the CPU, memory communicating with the CPU, and an UART for communication with a data device external to the vigilance monitor;

wherein the ambient environmental sensors include a light level sensor coupled to the A/D converter to communicate with the CPU, the source of stimuli includes a visual source of stimulation and an aural source of stimulation which are coupled to the digital I/O circuit to communicate with the CPU, and e) means for controlling the presentation of the stimuli to the subject, for detecting subject initiated response signals to the stimuli, for detecting the sensed environmental signals, for converting the environmental signals and the response signals to data values, and for controlling storage of the data values in a data memory.

2. A human subject vigilance monitor comprising:

a) a human subject stimulator, said stimulator having a first state corresponding to the absence of an applied stimulus to a human subject, and a second state corresponding to the presence of an applied stimulus to a human subject; and b) a human subject sensor, said sensor producing an output signal corresponding to said subject's volitional response to said applied stimulus; and c) an electronic controller, said controller having a first information input comprising information contained in said human subject sensor output signal, said controller having an output signal, said states of said stimulator determined by said output signal of said controller, said controller processing the timing relationship between said controller output signal to said first information input signal from said human subject sensor in accordance with a stored program, and producing information related to a subject's vigilance; and d) a means for using said information related to a subject's vigilance for signalling that a subject's vigilance has fallen below a desirable level.

3. A human subject vigilance monitor comprising:

a) a human subject stimulator, said stimulator having a first state corresponding to the absence of an applied stimulus to a human subject, and a second state corresponding to the presence of an applied stimulus to a human subject; and b) a human subject sensor, said sensor producing an output signal corresponding to a subject's volitional response to said applied stimulus; and c) an ambient environmental sensor, said sensor having an output signal responsive to a measured environmental condition; and d) an electronic controller, said controller having a first information input comprising information contained in said human subject sensor output signal, and a second input comprising information contained in said ambient environmental sensor output signal, said controller having an output signal, said states of said stimulator determined by said output signal of said controller, said controller processing the timing relationship between said controller output signal to said first information input signal from said human subject sensor with said second input signal in accordance with a stored program, producing information related to a subject's vigilance, and storing said produced information related to a subject's vigilance with said environmental information as a function of time; and e) a means for using said information related to a subject's vigilance for signalling that a subject's vigilance has fallen below a desirable level.

4. A human subject vigilance monitor comprising:

a) a human subject stimulator, said stimulator having a first state corresponding to the absence of an applied stimulus to a human subject, and a second state corresponding to the presence of an applied stimulus to a human subject; and b) a motion sensor for coupling to a human subject, said motion sensor generating an activity level signal related to the volitional activity of a subject as a volitional activity information output of said sensor; and c) an electronic controller, said controller having a first information input comprising information contained in said volitional activity output, said controller having an output signal, said states of said stimulator determined by said output signal of said controller, said controller processing said first input in accordance with a stored program and producing information related to a subject's vigilance; and d) a means for using said information related to a subject's vigilance for signalling that a subject's vigilance has fallen below a desirable level.

5. The vigilance monitor system of claim 3 wherein the ambient environmental sensor is a sound level sensor.

6. The vigilance monitor system of claim 3 wherein the ambient environmental sensor is a temperature sensor.

7. The vigilance monitor system of claim 3 wherein the ambient environmental sensor is a toxic gas sensor.

8. The vigilance monitor system of claim 2 further comprising a motion sensor coupled to the subject, said motion sensor generating an activity level signal related to the volitional activity of said subject as a volitional activity information input to said controller, said controller further processing said volitional activity input and producing information related to the subject's vigilance.

9. The vigilance monitor system of claim 2 wherein said human subject stimulator comprises a source of aural stimulation.

10. The vigilance monitor system of claim 9 wherein said source of aural stimulation is adapted to signal an alarm condition.

11. The vigilance monitor system of claim 2 wherein said human subject stimulator comprises a source of visual stimulation.

12. The vigilance monitor system of claim 11 wherein said source of visual stimulation is adapted to signal an alarm condition.

13. The vigilance monitor system of claim 11 wherein said source of visual stimulation comprises a plurality of differentially coded light sources.

14. The vigilance monitor system of claim 2 wherein said human subject sensor comprises a switch having normally open state, and a closed state, said states of said switch affecting said sensor's output signal.

15. The vigilance monitor system of claim 14 wherein said human subject sensor further comprises additional differentially coded switches, said states of said switches determining said sensor's output signal.

16. The method of operating a human subject vigilance monitor, said monitor having environmental sensors, volitional response sensors for detecting subject initiated volitional responses to a plurality of stimuli, and a controller including provision for a program instruction set therein, comprising the steps of:

a) activating said monitor with a START routine;

b) initializing said monitor with an INITIALIZE routine, including providing said monitor with a program instruction set initiating operation of said monitor and control of said program instruction set;

c) controlling presentation of visual and aural stimuli to a subject;

d) controlling measurement and data collection from said environmental sensors;

e) controlling data collection from said subject initiated volitional response sensors; and storing the collected environmental sensor data and the collected response data in a memory storage.

17. The method of claim 16 wherein presentation of said stimuli are on a random basis.

18. The method of claim 16 wherein presentation of said stimuli is at predetermined time intervals.

19. The method of claim 16, wherein presentation of stimuli is timed until a response signal is generated representing a sense/response time interval, further including the step of converting the sense/response time interval into a data value and storing said data value in said memory storage.

20. The method of claim 16, wherein said monitor further comprises an activity level sensor, further comprising the steps of:

a) controlling measurement and data collection from said activity level sensor;

b) presenting a particular timed stimulus; and c) storing the activity level data for a predetermined period before and after receiving a predetermined response to said particular timed stimulus.

21. The method of claim 16, wherein presentation of stimuli is timed to adjust circadian synchronization of a subject.

22. The method of claim 16, wherein said environmental data is evaluated under said program instruction set control, related environmental factors are converted to data values reflecting the relation of said environmental data, and then said data values reflecting the relation of said environmental data are stored.

23. The method of claim 16, wherein said presentation of visual and aural stimuli to a subject is dependent on said collected environmental sensor data.

24. The method of claim 16, wherein a response to a stimulus is timed and compared with a predetermined time interval, followed by the added step of varying the stimulus to increase vigilance of a subject.

25. The method of claim 16, wherein a response to a stimulus is timed and compared with a redetermined time interval, followed by the added step of varying the stimulus to effect Circadian synchronization adjustment of a subject.

26. The vigilance monitor of claim 2 further including means for determining reduced vigilance and for increasing the frequency of said second state until vigilance is restored to a desired level.

27. The vigilance monitor of claim 2 further comprising a housing, said housing containing said human subject stimulator, said human subject sensor, said electronic controller, and said means for using said information related to a subject's vigilance.

28. The vigilance monitor of claim 27 further comprising means for attaching said vigilance monitor to a human subject.

29. The vigilance monitor of claim 28 wherein said means for attaching said vigilance monitor to a human subject comprises a wristband attached to said housing, so that a human subject may affix said vigilance monitor to his wrist.

30. The vigilance monitor of claim 4 further comprising a housing, said housing containing said human subject stimulator, said motion sensor, said electronic controller, and said means for using said information related to a subject's vigilance, said housing having a wristband attached thereto for affixing said vigilance monitor system to the wrist of a human subject.

31. The vigilance monitor of claim 2 further comprising means for recording the subject's vigilance for later retrieval.

32. The vigilance monitor of claim 4 further comprising means for recording the subject's vigilance for later retrieval.

33. An article of manufacture for evaluating memory abilities or performance of a user by presenting a simple mental, complex mental, or psychomotor test to the user comprising:

a) a first switch having a normally open state and a closed state, and a second switch having a normally open state and a closed state, for interfacing with a user;

b) a source of a first type of stimulus to a user;

c) a source of a second type of stimulus to a user;

d) instruction means for controlling presentation of said first and second type of stimuli to a user;

e) instruction means for causing the detection of when either or both of said switches are moved into said closed state and storing the time and sequence of said closed state of each switch for later retrieval;

f) instruction means for determining deviation of time and sequence of said closed states of each switch from stored values;

g) instruction means for alerting a user of a deviation of time and sequence above a prescribed limit.

34. The article of manufacture claimed in claim 33 wherein said instruction means for controlling presentation of said first and second type of stimuli to said user, controls said presentation at preset times of a day.

35. The article of manufacture claimed in claim 33 wherein said instruction means for controlling presentation of said first and second type of stimuli to said user, increases the frequency of said presentation to a user based on magnitude of time deviation and the number of sequence deviations from said stored values.

36. The article of manufacture claimed in claim 33 wherein said first type of stimulus is an audible tone of a first duration, and said second type of stimulus is an audible tone of a second duration.

37. The article of manufacture claimed in claim 33 wherein said first type of stimulus is an audible tone of a first frequency, and said second type of stimulus is an audible tone of a second frequency.

38. The article of manufacture claimed in claim 33 wherein said first type of stimulus is a first light source, and said second type of stimulus is a second light source.

39. The article of manufacture claimed in claim 33 wherein said first type of stimulus is a light of a first color, and said second type of stimulus is a light of a second color.

40. The article of manufacture claimed in claim 33 wherein said first type of stimulus is a sequence of different colored light flashes embedded in a longer sequence of different colored light flashes.

* * * * *